(12) United States Patent
Sun

(10) Patent No.: US 8,426,446 B2
(45) Date of Patent: Apr. 23, 2013

(54) ACRYLAMIDE DERIVATIVE AND USE THEREOF IN MANUFACTURE OF MEDICAMENT

(75) Inventor: Shuping Sun, Beijing (CN)

(73) Assignees: Beijing Shiqiao Biopharm Co. Ltd., Beijing (CN); Beijing Jiashilianbo Pharm Sci & Tech Co. Ltd., Beijing (CN)

( * ) Notice: Subject to any disclaimer, the term of this patent is extended or adjusted under 35 U.S.C. 154(b) by 0 days.

(21) Appl. No.: 13/320,039

(22) PCT Filed: Apr. 27, 2010

(86) PCT No.: PCT/CN2010/072245
§ 371 (c)(1),
(2), (4) Date: Jan. 21, 2012

(87) PCT Pub. No.: WO2010/130178
PCT Pub. Date: Nov. 18, 2010

(65) Prior Publication Data
US 2012/0116075 A1    May 10, 2012

(30) Foreign Application Priority Data

May 12, 2009 (CN) .......................... 2009 1 0136362
Sep. 3, 2009 (CN) .......................... 2009 1 0170110

(51) Int. Cl.
*A01N 43/40* (2006.01)
*A61K 31/44* (2006.01)
(52) U.S. Cl.
USPC ........... 514/332; 544/333; 544/335; 546/309; 546/261; 514/256
(58) Field of Classification Search ................. 544/333, 544/335; 546/261, 309; 514/256, 332
See application file for complete search history.

(56) References Cited

U.S. PATENT DOCUMENTS 7,550,490 B2 *   6/2009  Lu et al. .......................... 514/357

FOREIGN PATENT DOCUMENTS

| WO | 9748696 A1 | 12/1997 |
| WO | 0168585 A1 | 9/2001 |
| WO | 2008025857 A2 | 3/2008 |

OTHER PUBLICATIONS

International Search Report for PCT/CN2010/072245 dated Jun. 17, 2010.

* cited by examiner

*Primary Examiner* — James O Wilson
*Assistant Examiner* — Alexander R Pagano
(74) *Attorney, Agent, or Firm* — Ling Wu; Stephen Yang; Ling and Yang Intellectual Property

(57) ABSTRACT

An acrylamide derivative represented by formula (I), pharmaceutically acceptable salts and solvates thereof, as well as a medicament containing said acrylamide derivative or its pharmaceutically acceptable salts as the active ingredient, which can be used to treat disorders associated with tyrosine kinase especially Bcr-Abl, including proliferative disorders such as cancers, and inflammation and the like are provided.

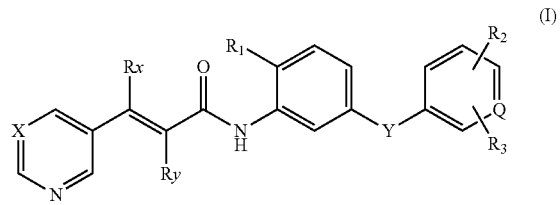

19 Claims, No Drawings

ACRYLAMIDE DERIVATIVE AND USE THEREOF IN MANUFACTURE OF MEDICAMENT

FIELD OF THE INVENTION

This invention relates to a sort of acrylamide derivatives, the salts of the compounds and a medicament using the compounds or their salts as active ingredients, which can be used for treating diseases associated with tyrosine kinase, especially Bcr-Abl, including proliferative diseases such as cancers, inflammatory diseases, etc.

THE BACKGROUND OF THE INVENTION

Methionine kinases are classified into two categories: tyrosine kinases and serine/serine-threonine protein kinases.

Among protein kinases, it is generally believed that the tyrosine protein kinases have played an important role in a number of cell functions, in particular, participating in cell signaling. A number of research findings indicate that the tyrosine protein kinases have played an indispensable important role in cell proliferation, canceration and fission process.

Tyrosine protein kinases are classified into two categories: receptor and non-receptor tyrosine protein kinases. Receptor tyrosine protein kinases generally consist of those that are extracellular, across the cell membrane and intracellular, while non-receptor tyrosine protein kinases are completely intracellular.

So far, approximately 20 families of receptor tyrosine protein kinases have been found, among which, HER subfamily includes EGFR, HER2, HER3 and HER4, and the ligands binding to the receptors within this subfamily includes epidermal growth factor, TGF-β, HB-EGF, etc. Another subfamily is the tyrosine protein kinases associated with insulin receptors, including INS-R, IGF-IR, and IR-R. PDGF subfamily comprises PDGFRα, PDGFRβ, CSFIR, C-kit and FLK-II. In addition, there is another class of FLK subfamily comprising KDR, FLK-1, FLK-4, and Flt-1. Due to the structural and functional similarity, the two subfamilies—PFDG and FLK are usually designated into one subfamily.

There are many subfamilies for non-cell tyrosine protein kinases, such as Abl, Src, Frk, Btk, Csk, and ZAP-70, etc. Each subfamily can be further classified into different subsubfamilies. For example, Src is one of the largest subfamilies and includes Src, Yes, Fyn, Lyn, Lck, Blk, Hck, Fgt, and Yrk. This subfamily is extensively considered to be closely related to tumor formation.

The increase in the activity of tyrosine protein kinases like Abl is directly associated with the chronic myeloid leukemia (CML) in blood. During the research on the pathogenesis of CML, Nowell et al reported the discovery of the abnormal minisome named Ph[1] chromosome, presently referred to as Ph chromosome, in the cells of two CML patients for the first time in Philadelphia, USA in 1960. Along with the development of molecular biology, the molecular characteristics of Ph chromosome and its role in pathogenesis are increasingly clear. That is resulted from the translocation of No. 9 and No. 22 chromosomes, wherein the protooncogene c-ABL is broken down at the end of the long arm of No. 9 chromosome (q34) and fused with the breakpoint cluster region (M-bCR gene) at the end of long arm of No. 22 chromosome (q11). C-ABL protooncogene is 230 kb long, normally encodes a 145 kD protein with tyrosine kinase activity, and functions to regulate the expression of growth factor receptors (colony stimulating factor receptor, platelet derived growth factor, and epidermal growth factor). The breakpoint of No. 9 chromosome is generally located at the 5/end of the second exon of c-ABL gene. The second exon and its subsequent sequence are translocated to a breakpoint (BCR gene) cluster region of No. 22 chromosome having unknown functions, and spliced into a new fusion gene (Bcr-Abl gene), the latter translates a Bcr-Abl fusion protein product P210 (Bcr-Abl protein) the molecular weight of which is 21.0 kD. P210 demonstrates abnormal tyrosine kinase activity as compared with P145 encoded by c-ABL. Relevant research has already indicated that pathogenesis of CML is closely related to Bcr-Abl fusion gene and its translation product Bcr-Abl protein can facilitate cell proliferation and inhibit cell apoptosis. After self-phosphorylation, Bcr-Abl protein (P210) will provide binding sites for a series of adapter protein molecules such as Grb-2, SHC, CRKL, etc., so as to activate RAS (MAPK) signal pathway or JAK/STAT signal pathway and up-regulate the expression of intranuclear gene c-myc, bcl-2, c-fos, etc. The abnormalities of these signal pathways lead to canceration, abnormal proliferation, differentiation and inhibition of apoptosis, of bone-marrow precursor cells. Thus it can be seen that the existence of Bcr-Abl fusion gene and its chimeric transcript is an extremely important pathogenic factor and very clear prognostic marker of CML, i.e. Bcr-Abl gene is an important target gene to cure CML.

Imatinib (STI571) is a tyrosine kinase specific inhibitor marketed by Novartis Corporation. Imatinib inhibits the self-phosphorylation and substrate phosphorylation of Bcr-Abl protein by occupying the ATP binding site of Bcr-Abl fusion protein, so as to inhibit Bcr-Abl positive cell proliferation or cause apoptosis. Recent researches demonstrate that imatinib not only inhibits the activity of Bcr-Abl kinase, but also inhibits tyrosine kinase activities of stem cell factor receptor (KIT), platelet derived growth factor receptor A (PDGFR-A), and platelet derived growth factor receptor B (PDGFR-B). As a result, it is also used for the treatment of tumor such as gastrointestinal stromal tumors.

Along with the generalization of this drug in clinical applications, however, drug resistance against imatinib has occurred in increasing cases. There are a wide variety of drug resistance mechanisms against imatinib, (1) Bcr-Abl gene mutation; (2) the over-expression of Bcr-Abl protein in CML cell exceeds the competitive binding capacity of imatinib; (3) the reduction in the concentration of intracellular imatinib may be related to the increase of the expression level of glycoprotein (P-gP) on tumor cell membrane. In fact, more than 50% of drug resistance is attributed to one or more amino acid mutations of Bcr-Abl fusion protein, leading to the inability of imatinib to bind to ATB binding site of the fusion protein. One of the effective ways for overcoming the drug resistance against the existing drugs is to develop tyrosine protein kinase inhibitor with a new structure.

CONTENT OF THE INVENTION

This invention provides acrylamide derivatives that are selective tyrosine to protein kinase inhibitors. Their main use is to provide an anti-cancer effect by inhibiting the activity of tyrosine protein kinase. The main tyrosine protein kinases inhibited by this class of compounds are Abl, P38β, PDGF-R, C-Kit, etc. Of course, the possibility for this class of compounds to inhibit other disease-related protein kinases can also not be excluded.

The purpose of this invention is to provide new acrylamide derivatives and their salts or solvates.

Another purpose of this invention is to provide a method for preparation of the derivatives.

The third purpose of this invention is to provide a pharmaceutical composition containing the derivatives.

The fourth purpose of the invention is to provide the use of the derivatives.

Specifically, this invention provides an acrylamide derivative having the structure of Formula (I), or pharmaceutically acceptable salts or solvates thereof:

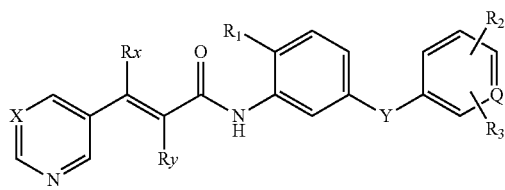

Formula (I)

wherein:
$R_1$ is $C_1$-$C_4$ alkyl, preferably methyl,
X is CH or N;
Q is CH or N;
Y is formamido

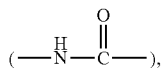

carbamoyl

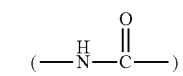

or ureido

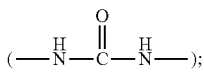

$R_x$ and $R_y$ are independently selected from hydrogen and $C_1$-$C_4$ respectively;

$R_2$ and $R_3$ are each independently hydrogen, halogen, $C_1$-$C_4$ alkyl, $C_1$-$C_4$ alkoxy, $C_1$-$C_4$ alkylamino, alkyl)amino, heterocyclyl, and non-heterocyclyl; these groups, except hydrogen or halogen, can be further optionally substituted with halogen, $C_1$-$C_4$ alkyl, $C_1$-$C_4$ alkoxy, alkyl)amino, and heterocyclyl; these substituents may be further substituted with halogen, $C_1$-$C_4$ alkyl, $C_1$-$C_4$ alkoxy, alkylamino, di-(C alkyl)amino, heterocyclyl, and non-heterocyclyl; the heterocyclyl as described herein may be selected from 5 or 6 member heterocyclyl. Said heterocyclyl containing one or more heteroatoms selected from oxygen, nitrogen or sulfur is either aromatic or non-aromatic. Non-limiting examples include piperazinyl, piperidyl, pyrrolidinyl, morpholinyl, or pyridyl, pyrrolyl, oxazolyl, imidazolyl, or pyrimidinyl, etc. The non-heterocyclyl may be selected from 5 or 6 member non-heterocyclyl, and is either aromatic or non-aromatic, such as benzene, etc.

Preferably, this invention provides a compound having the structure of Formula (II), or pharmaceutically acceptable salts or solvates thereof

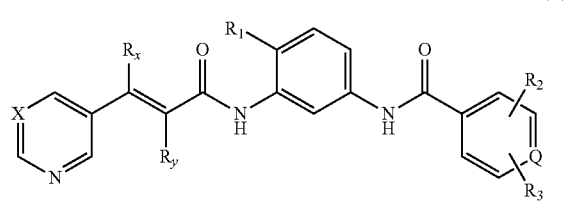

Formula (II)

wherein, $R_1$, $R_2$, $R_3$, $R_x$, $R_y$, X, and Q are as described in the structure of Formula (I).

More specifically, this invention provides the compounds having the structure of Formula (II), or pharmaceutically acceptable salts or solvates thereof.

N-(4-methyl-3-(3-(pyridin-3-yl)acrylamido)phenyl)-4-methyl benzamide;

N-(4-methyl-3-(3-(pyridin-3-yl)acrylamido)phenyl)-4-fluorobenzamide;

N-(4-methyl-3-(3-(pyridin-3-yl)acrylamido)phenyl)-2,4-difluoro benzamide;

N-(4-methyl-3-(3-pyridin-3-yl)amido)phenyl)-3-(trifluoromethyl)acryl benzamide;

N-(4-methyl-3-(3-(pyridin-3-yl)acrylamido)phenyl)-3-chloro-4-methyl benzamide;

N-(4-methyl-3-(3-(pyridin-3-yl)acrylamido)phenyl)-4-fluoro-3-(trifluoromethyl)benzamide;

N-(4-methyl-3-(3-(pyridin-3-yl)acrylamido)phenyl)-2,4-dichloro benzamide;

N-(4-methyl-3-(3-(pyridin-3-yl)acrylamido)phenyl)-3,5-bis-(trifluoromethyl)benzamide;

N-(4-methyl-3-(3-(pyridin-3-yl)acrylamido)phenyl)-3-(trifluoromethyl)-4-methyl benzamide;

N-(4-methyl-3-(3-(pyridin-3-yl)acrylamido)phenyl)-3-(trifluoromethyl)benzamide;

N-(4-methyl-3-(3-(pyridin-3-yl)acrylamido)phenyl)-4-((4-methylpiperazin-1-yl)methyl)benzamide;

N-(4-methyl-3-(3-pyridin-3-acrylamido)phenyl)-4-((cis-3,5-dimethyl piperazin-1-yl)methyl)benzamide;

N-(4-methyl-3-(3-(pyridin-3-yl)acrylamido)phenyl)-4-((4-ethylpiperazin-1-yl)methyl)benzamide;

N-(4-methyl-3-(3-(pyridin-3-yl)acrylamido)phenyl)-4-((4-piperidin-1-yl)methyl)benzamide;

N-(4-methyl-3-(3-(pyridin-3-yl)acrylamido)phenyl)-4-(morpholin-4-yl methyl)benzamide;

N-(4-methyl-3-(3-(pyridin-3-yl)acrylamido)phenyl)-4-((4-methyl-1,4-homopiperazin-1-yl)methyl)benzamide;

N-(4-methyl-3-(3-(pyridin-3-yl)acrylamido)phenyl)-4-((diethylamino)methyl)benzamide;

N-(4-methyl-3-(3-(pyridin-3-yl)acrylamido)phenyl)-4-((4-hydroxyethyl to piperazin-1-yl)methyl)benzamide;

N-(4-methyl-3-(3-(pyridin-3-yl)acrylamido)phenyl)-4-((4-methylpiperazin-1-yl)methyl)-3-(trifluoromethyl)benzamide;

N-(4-methyl-3-(3-(pyridin-3-yl)acrylamido)phenyl)-4-((4-ethylpiperazin-1-yl)methyl)-3-(trifluoromethyl)benzamide;

N-(4-methyl-3-(3-(pyridin-3-yl)acrylamido)phenyl)-4-(morpholin-4-yl methyl)-3-(trifluoromethyl)benzamide;

N-(4-methyl-3-(3-(pyridin-3-yl)acrylamido)phenyl)-4-(((R)-3-(dimethylamino)pyrrolidin-1-yl)methyl)-3-(trifluoromethyl)benzamide:

N-(4-methyl-3-(3-(pyridin-3-yl)acrylamido)phenyl)-4-(((S)-3-(dimethyl amino)pyrrolidin-1-yl)methyl)-3-(trifluoromethyl)benzamide;

N-(4-methyl-3-(3-(pyridin-3-yl)acrylamido)phenyl)-4-((3-(dimethylamino)pyrrolidin-1-yl)methyl)-3-(trifluoromethyl)benzamide;
N-(4-methyl-3-(3-(pyridin-3-yl)acrylamido)phenyl)-4-((4-methyl-1,4-homopiperazin-1-yl)methyl)-3-(trifluoromethyl)benzamide;
N-(4-methyl-3-(3-(pyridin-3-yl)acrylamido)phenyl)-4-((4-methylpiperazin-1-yl)methyl)-3-bromobenzamide;
N-(4-methyl-3-(3-pyridin-3-yl)acrylamido)phenyl)-4-((cis-3,5-dimethyl piperazin-1-yl)methyl)-3-bromobenzamide;
N-(4-methyl-3-(3-(pyridin-3-yl)acrylamido)phenyl)-4-((4-ethylpiperazin-1-yl)methyl)-3-bromobenzamide:
N-(4-methyl-3-(3-(pyridin-3-yl)acrylamido)phenyl)-4-(morpholin-4-yl methyl)-3-bromobenzamide;
N-(4-methyl-3-(3-(pyridin-3-yl)acrylamido)phenyl)-(4-((4-methyl-1,4-homopiperazin-1-yl)methyl)-3-bromobenzamide;
N-(4-methyl-3-(pyrimidin-5-yl)acrylamido)phenyl)-3,5-bis-(trifluoro methyl)benzamide;
N-(4-methyl-3-(3-(pyrimidin-5-yl)acrylamido)phenyl)-4-methyl-3-(trifluoromethyl)benzamide;
N-(4-methyl-3-(3-(pyrimidin-5-yl)acrylamido)phenyl)-5-fluoro-3-(trifluoromethyl)benzamide;
N-(4-methyl-3-(3-(pyrimidin-5-yl)acrylamido)phenyl)-4-methyl benzamide;
N-(4-methyl-3-(3-(pyrimidin-5-yl)acrylamido)phenyl)-4-fluorobenzamide
N-(4-methyl-3-(3-(pyrimidin-5-yl)acrylamido)phenyl)-2,4-difluoro benzamide;
N-(4-methyl-3-(3-(pyrimidin-5-yl)acrylamido)phenyl)-2,4-dichloro benzamide;
N-(4-methyl-3-(3-(pyrimidin-5-yl)acrylamido)phenyl)-4-((4-methyl piperazin-1-yl)methyl)benzamide;
N-(4-methyl-3-(3-(pyrimidin-5-yl)acrylamido)phenyl)-4-((4-methyl piperazin-1-yl)methyl)-3-(trifluoromethyl)benzamide;
N-(4-methyl-3-(3-(pyrimidin-5-yl)acrylamido)phenyl)-4-((4-ethyl piperazin-1-yl)methyl)-3-(trifluoromethyl)benzamide;
N-(4-methyl-3-(3-(pyrimidin-5-yl)acrylamido)phenyl)-4-(morpholin-4-yl methyl)-3-(trifluoromethyl)benzamide;
N-(4-methyl-3-(3-(pyrimidin-5-yl)acrylamido)phenyl)-4-(((R)-3-(dimethylamino)pyrrolidin-1-yl)methyl)-3-(trifluoromethyl)benzamide;
N-(4-methyl-3-(3-(pyrimidin-5-yl)acrylamido)phenyl)-4-(((S)-3-(dimethyl amino)pyrrolidin-1-yl)methyl)-3-(trifluoromethyl)benzamide;
N-(4-methyl-3-(3-(pyrimidin-5-yl)acrylamido)phenyl)-4-((3-(dimethylamino)pyrrolidin-1-yl)methyl)-3-(trifluoromethyl)benzamide:
N-(4-methyl-3-(3-(pyrimidin-5-yl)acrylamido)phenyl)-4-((4-methyl-1,4-homopiperazin-1-yl)methyl)-3-(trifluoromethyl)benzamide;
N-(4-methyl-3-(3-(pyrimidin-5-yl)acrylamido)phenyl)-4-((4-methyl piperazin-1-yl)methyl)-3-bromobenzamide;
N-(4-methyl-3-(3-(pyrimidin-5-yl)acrylamido)phenyl)-4-((4-methyl piperazin-1-yl)methyl)-3-chlorobenzamide;
N-(4-methyl-3-(3-(pyrimidin-5-yl)acrylamido)phenyl)-4-(morpholin-4-yl methyl)-3-bromobenzamide;
N-(4-methyl-3-(3-(pyrimidin-5-yl)acrylamido)phenyl)-4-((4-methyl-1,4-homopiperazin-1-yl)methyl)-3-bromobenzamide;
N-((3-bromo-4-methyl)phenyl)-4-methyl-3-(3-(pyrimidin-5-yl)acrylamido)benzamide;
N-((3-chloro-4-methyl)phenyl)-4-methyl-3-(3-(pyrimidin-5-yl)acrylamido)benzamide;
N-((3-bromo-4-methyl)phenyl)-4-methyl-3-(3-(pyridin-3-yl)acrylamido)benzamide.

Preferably, this invention provides a compound having the structure of Formula (III), or pharmaceutically acceptable salts or solvates thereof:

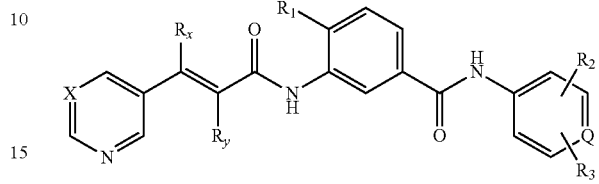

Formula (III)

wherein, $R_1$, $R_2$, $R_3$, $R_x$, $R_y$, X, and Q are as described in the structure of Formula (I).

More preferably, this invention provides the compounds having the structure of Formula (III) or pharmaceutically acceptable salts or solvates thereof:
N-(3-chloro-4-fluorophenyl)-4-methyl-3-(3-(pyridin-3-yl)acrylamido)benzamide;
N-(3,5-di-(trifluoromethyl)phenyl)-4-methyl-3-(3-(pyridin-3-yl)acrylamido)benzamide;
N-(2,6-dimethyl)-4-methyl-3-(3-(pyridin-3-yl)acrylamido)benzamide;
N-(3-(trifluoromethyl)phenyl)-4-methyl-3-(3-(pyridin-3-yl)acrylamido)benzamide;
N-(4-bromo-2-fluorophenyl)-4-methyl-3-(3-(pyridin-3-yl)acrylamido)benzamide;
N-(4-(trifluoromethoxy)phenyl)-4-methyl-3-(3-(pyridin-3-yl)acrylamido)benzamide;
N-(4-(methoxy)phenyl)-4-methyl-3-(3-(pyridin-3-yl)acrylamido)benzamide;
N-(4-(4-methyl-1H-imidazol-1-yl)-3-(trifluoromethyl)phenyl)-4-methyl-3-(3-(pyridin-3-yl)acrylamido)benzamide;
N-(3,4-dichlorophenyl)-4-methyl-3-(3-(pyridin-3-yl)acrylamido)benzamide;
N-(2-chloro-5-(trifluoromethyl)phenyl)-4-methyl-3-(3-(pyridin-3-yl)acrylamido)benzamide;
N-(4-chloro-3-(trifluoromethyl)phenyl)-4-methyl-3-(3-(pyridin-3-yl)acrylamido)benzamide;
N-(3,4-dimethoxyphenyl)-4-methyl-3-(3-(pyridin-3-yl)acrylamido)benzamide;
N-(4-fluoro-3-(trifluoromethyl)phenyl)-4-methyl-3-(3-(pyridin-3-yl)acrylamido)benzamide;
N-(3-fluoro-4-methylphenyl)-4-methyl-3-(3-(pyridin-3-yl)acrylamido)benzamide;
N-(4-methyl-3-(trifluoromethyl)phenyl)-4-methyl-3-(3-(pyridin-3-yl)acrylamido)benzamide;
N-(3-(4-methyl-1H-imidazol-1-yl)-5-(trifluoromethyl)phenyl)-4-methyl-3-(3-(pyridin-3-yl)acrylamido)benzamide;
N-(4-(morpholin-4-ylmethyl)-3-(trifluoromethyl)phenyl)-4-methyl-3-(3-(pyridin-3-yl)acrylamido)benzamide;
N-(4-fluorophenyl)-4-methyl-3-(3-(pyridin-3-yl)acrylamido)benzamide;
N-(4-(methyl)phenyl)-4-methyl-3-(3-(pyridin-3-yl)acrylamido)benzamide;
N-(2-chloro-6-methylphenyl)-4-methyl-3-(3-(pyridin-3-yl)acrylamido)benzamide;
N-(3-fluorophenyl)-4-methyl-3-(3-(pyridin-3-yl)acrylamido)benzamide;
N-(4-(morpholin-4-yl)-3-(trifluoromethyl)phenyl)-4-methyl-3-(3-(pyridin-3-yl)acrylamido)benzamide;

N-((3-(piperidin-1-yl)methyl)phenyl)-4-methyl-3-(3-(pyridin-3-yl)acrylamido)benzamide;
N-(4-(4-methylpiperazin-1-yl)-3-(trifluoromethyl)phenyl)-4-methyl-3-(3-(pyridin-3-yl)acrylamido)benzamide;
N-(3-((4-methylpiperazin-1-yl)methyl)phenyl)-4-methyl-3-(3-(pyridin-3-yl)acrylamido)benzamide;
N-(4-(morpholin-4-ylmethyl)phenyl)-4-methyl-3-(3-(pyridin-3-yl)acrylamido)benzamide;
N-(4-(4-ethylpiperazin-1-yl)-3-(trifluoromethyl)phenyl)-4-methyl-3-(3-(pyridin-3-yl)acrylamido)benzamide;
N-(4-methyl-3-(trifluoromethyl)phenyl)-4-methyl-3-(3-(pyrimidin-5-yl)acrylamido)benzamide;
N-(4-(morpholin-4-yl)-3-(trifluoromethyl)phenyl)-4-methyl-3-(3-(pyrimidin-5-yl)acrylamido)benzamide;
N-(4-chloro-3-(trifluoromethyl)phenyl)-4-methyl-3-(3-(pyrimidin-5-yl)acrylamido)benzamide;
N-(3-fluoro-4-dimethylphenyl)-4-methyl-3-(3-(pyrimidin-5-yl)acrylamido)benzamide;
N-(3-chloro-4-fluorophenyl)-4-methyl-3-(3-(pyrimidin-5-yl)acrylamido)benzamide;
N-(2-chloro-6-methylphenyl)-4-methyl-3-(3-(pyrimidin-5-yl)acrylamido)benzamide;
N-(3,4-dichlorophenyl)-4-methyl-3-(3-(pyrimidin-5-yl)acrylamido)benzamide;
N-(4-trifluoromethoxyphenyl)-4-methyl-3-(3-(pyrimidin-5-yl)acrylamido)benzamide;
N-(3-(4-methyl-1-imidazol-1-yl)-5-(trifluoromethyl)phenyl)-4-methyl-3-(3-(pyrimidin-5-yl)acrylamido)benzamide;
N-(4-methylphenyl)-4-methyl-3-(3-(pyrimidin-5-yl)acrylamido)benzamide;
N-(4-fluorophenyl)-4-methyl-3-(3-(pyrimidin-5-yl)acrylamido)benzamide;
N-(4-bromo-2-fluorophenyl)-4-methyl-3-(3-(pyrimidin-5-yl)acrylamido)benzamide;
N-(3-(trifluoromethyl)phenyl)-4-methyl-3-(3-(pyrimidin-5-yl)acrylamido)benzamide;
N-(3-fluorophenyl)-4-methyl-3-(3-(pyrimidin-5-yl)acrylamido)benzamide;
N-(3,5-di-(trifluoromethyl)phenyl)-4-methyl-3-(3-(pyrimidin-5-yl)acrylamido)benzamide;
N-(4-fluoro-3-(trifluoromethyl)phenyl)-4-methyl-3-(3-(pyrimidin-5-yl)acrylamido)benzamide;
N-(4-(4-methylpiperazin-1-yl)-3-(trifluoromethyl)phenyl)-4-methyl-3-(3-(pyrimidin-5-yl)acrylamido)benzamide;
N-(4-(4-methyl-1H-imidazol-1-yl)-3-(trifluoromethyl)phenyl)-4-methyl-3-(3-(pyrimidin-5-yl)acrylamido)benzamide.

Preferably, this invention provides a compound having the structure of Formula (IV) or pharmaceutically acceptable salts or solvates thereof:

Formula (IV)

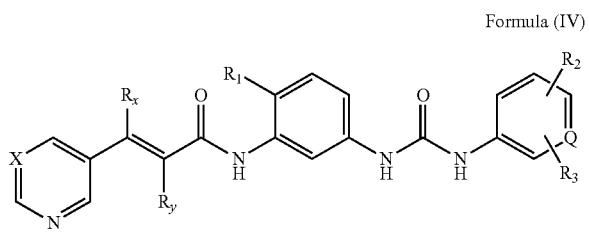

wherein, $R_1$, $R_2$, $R_3$, $R_x$, $R_y$, X, and Q are as described in the structure of Formula (I).

More preferably, this invention provides the compounds having the structure of Formula (IV), or pharmaceutically acceptable salts or solvates thereof:

N-(5-(3-(3-trifluoromethyl)phenyl)ureido)-2-methylphenyl)-3-(pyridin-3-yl)acrylamide;
N-(5-(3-(2-chloro-5-(trifluoromethyl)phenyl)ureido)-2-methylphenyl)-3-(pyridin-3-yl)acrylamide;
N-(5-(3-(4-(trifluoromethoxy)phenyl)ureido)-2-methylphenyl)-3-(pyridin-3-yl)acrylamide;
N-(2-methyl-5-(3-(5-(methylisoxazol-3-yl)ureido)phenyl)-3-(pyridin-3-yl)acrylamide;
N-(5-(3-(3-chloro-4-fluorophenyl)ureido)-2-methylphenyl)-3-(pyridin-3-yl)acrylamide;
N-(5-(3-(5-bromo-2-fluorophenyl)ureido)-2-methylphenyl)-3-(pyridin-3-yl)acrylamide;
N-(5-(3-(4-methoxyphenyl)ureido)-2-methylphenyl)-3-(pyridin-3-yl)acrylamide;
N-(5-(3-(4-fluorophenyl)ureido)-2-methylphenyl)-3-(pyridin-3-yl)acrylamide;
N-(5-(3-(4-chloro-3-(trifluoromethyl)phenyl)ureido)-2-methylphenyl)-3-(pyridin-3-yl)acrylamide;
N-(5-(3-(4-bromo-3-(trifluoromethyl)phenyl)ureido)-2-methylphenyl)-3-(pyridin-3-yl)acrylamide;
N-(5-(3-(3-(trifluoromethyl)-4-fluorophenyl)ureido)-2-methylphenyl)-3-(pyridin-3-yl)acrylamide.

In the embodiments of this invention, the compounds of the invention include their cis-form structure, trans-form structure and mixtures thereof, unless otherwise stated.

In the embodiments provided by this invention, if the compounds of the invention contain a basic group, then they can form salts with acids. The salts of acrylamide derivatives can be prepared using the methods well known for those skilled in the art.

Typical acid addition salts include organic acid salts, inorganic acid salts, etc. Generally, commonly used organic acid salts include citrates, fumarates, oxalates, malates, lactates, sulfonates (such as camphorsulfonates, p-toluene sulfonates, mesylates, etc.) and the like; inorganic acid salts include halogen acid salts, sulfates, phosphates, nitrates, etc.

For example, they can form mesylates, or trifluoromethanesulfonates, with lower alkyl sulfonic acids such as methanesulfonic acid, trifluoromethanesulfonic acid, etc.; p-toluenesulfonates, benzenesulfonates, with aryl sulfonic acids such as benzenesulfonic acid or p-toluenesulfonic acid, etc.; corresponding salts with organic carboxylic acids, such as acetic acid, fumaric acid, tartaric acid, oxalic acid, maleic acid, malic acid, succinic acid or citric acid; and glutamates or aspartates with amino acids such as glutamic acid or aspartic acid; appropriate salts with inorganic acids, such as haloid acid (such as hydrofluoric acid, hydrobromic acid, hydriodic acid, hydrochloric acid), nitric acid, carbonic acid, sulfuric acid or phosphoric acid, etc.

In another aspect, this invention provides the method for preparing the compounds of Formula (I).

The compounds of Formula (I) were synthesized from the compounds of Formula (V) and compounds of Formula (VI) (as illustrated in Scheme 1):

Scheme 1
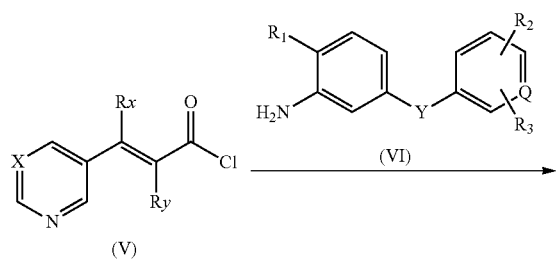
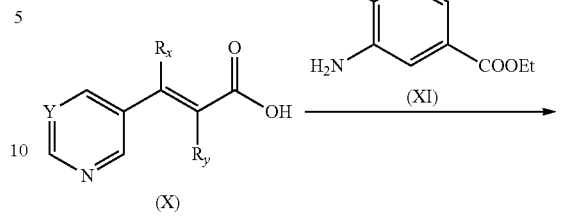
More specifically, the compounds of Formula (II) were synthesized using the following scheme (as illustrated in scheme 2):
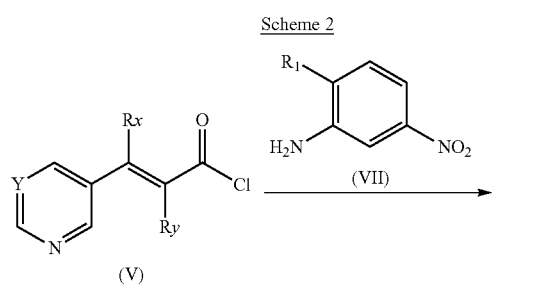
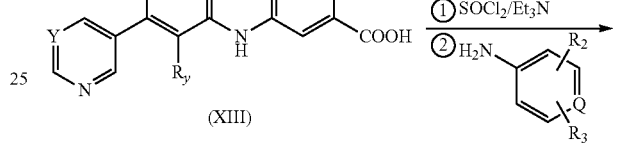
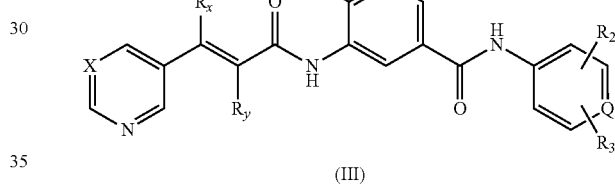
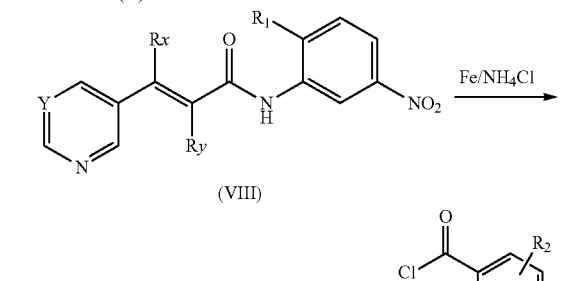
Scheme 4
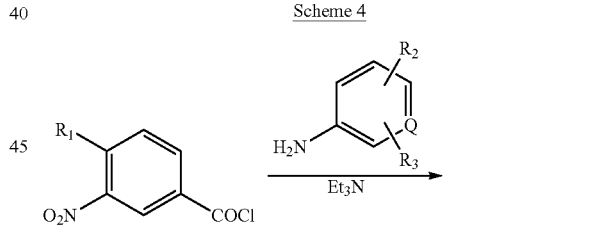
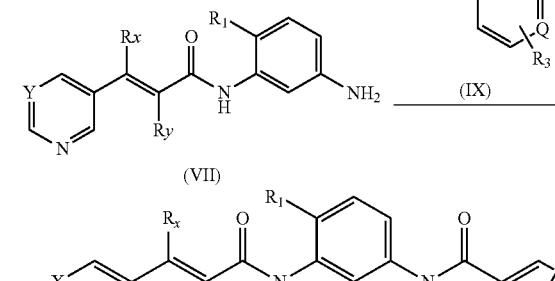
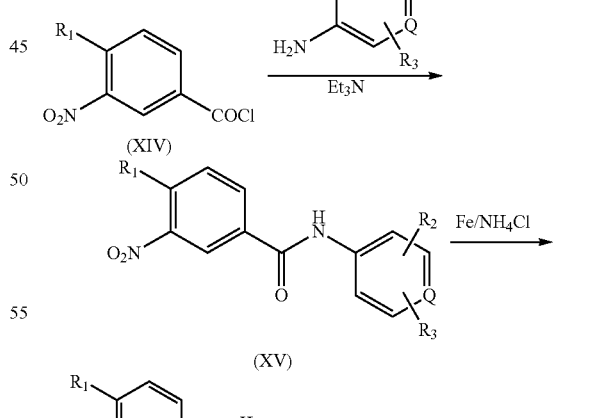
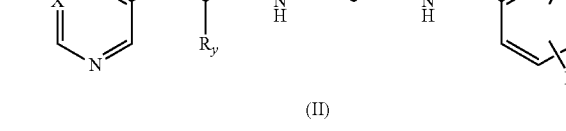
The compounds of Formula (III) were synthesized using the following route (as illustrated in scheme 3 or scheme 4):

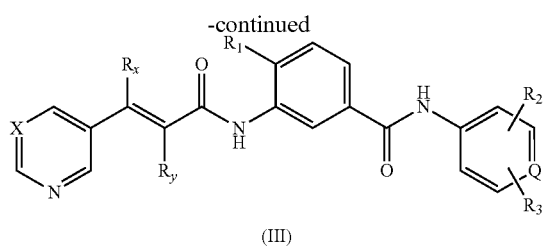

(III)

The compounds of Formula (IV) were synthesized using the scheme shown in scheme 5:

Scheme 5

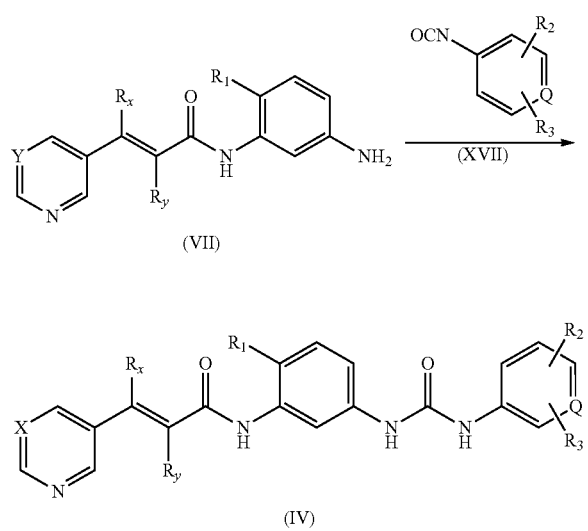

In the third aspect, this invention provides a medicament using the acrylamide derivative of this invention, or pharmaceutically acceptable salts or to solvates thereof as the active ingredients. The medicament can further include one or more pharmaceutically acceptable carriers, including conventional diluents, excipients, bulking agents, adhesives, wetting agents, disintegrants, absorption promoters, surfactants, absorption carriers, lubricants, etc. in the field of pharmacy. If necessary, flavouring agent, sweetener and the like may also be included. The medicament of the invention may be formulated into various forms such as tablets, powders, granules, capsules, oral liquids, and injectable preparations, and the like. The above dosage forms of the medicament can be prepared according to the conventional methods in the field of pharmacy.

In the fourth aspect, this invention provides a medicament for treating diseases relating to protein tyrosine kinase (PTK), especially Bcr-Abl, including proliferative diseases such as cancers and inflammatory diseases, etc.

By experiments, the inventor of this invention has proved that the to compounds of the invention have anti-proliferative and inhibitive effects on K562 and can be used in the drugs for treating psoriasis, leukemia or solid tumor associated with human or animal cell proliferation.

EMBODIMENTS OF THE INVENTION

The embodiments of the invention are illustrated by the following examples. Those skilled in the art should understand that any modification or replacement made to the corresponding technical features according to the teaching of the prior art are within the scope claimed by this invention.

Example 1

Synthesis of N-(4-methyl-3-(3-(pyridin-3-yl)acrylamido)phenyl)-4-methylbenzamide (Compound 1)

Step 1. Synthesis of 3-pyridin-3-ylacryloyl chloride hydrochloride

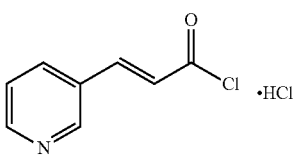 [SMILES: O=C(Cl)/C=C/c1cccnc1 ; Cl]

Triethylamine (0.5 ml) was added dropwise to a suspension of 3-pyridin-3-ylacrylic acid (5.0 g) in anhydrous dichloromethane (30 ml), and 6 ml of oxalyl chloride was added dropwise slowly in an ice-bath with the temperature no more than 5° C. After addition, the reaction was carried out for 30 min in an ice-bath, and then at room temperature overnight. The completion of reaction was indicated by TLC. The reaction mixture was concentrated under reduced pressure to give a white solid, which was left to stand at room temperature for 1 h, and used directly for the next step.

Step 2. Synthesis of N-(2-methyl-5-nitrophenyl)-3-pyridinylacrylamide

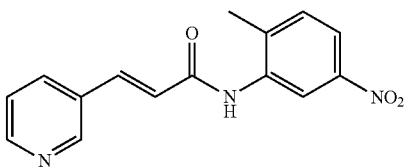

To a suspension of the product of step 1 (10.2 g) in anhydrous dichloromethane (250 ml), a solution of 2-methyl-5-nitroaniline (15.2 g) and triethylamine (21 ml, excess allowed) in dichloromethane (60 ml) was added dropwise slowly in an ice-bath with the temperature no more than 5° C. After to addition, the reaction was carried out for 30 min in an ice-bath, and then at room temperature for 3 h. The solution became clear yellow solution. The completion of the reaction was indicated by TLC. After that, potassium carbonate solution (10%) was added, and then the solid was precipitated, and filtered out. The filter cake was washed with water, and dried to give a pale-yellow powdered solid.

Step 3. Synthesis of (E)-N-(5-amino-2-methylphenyl)-3-pyridinyl acrylamide

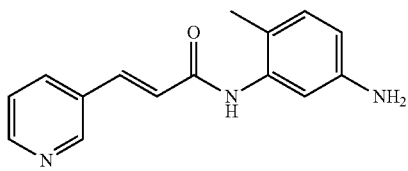 [SMILES: Cc1ccc([N+](=O)[O-])cc1NC(=O)/C=C/c1cccnc1]

8.6 g of the product of step 2 was added to 200 ml ethanol:water (v/v=3/1), then 13.6 g of iron powder and 5.0 g of ammonium chloride were added. After addition, the reaction mixture was heated to 70° C., and reacted for 30 min. The completion of reaction was indicated by TLC. Then the reaction mixture was filtered, washed with hot ethanol repeatedly, and concentrated under reduced pressure to give a yellow solid. 20 ml of potassium carbonate solution (10%) was added to the solid. The mixture was stirred, left to stand, filtered, and dried to give a solid.

Step 4. Synthesis of N-(4-methyl-3-(3-(pyridin-3-yl)acrylamido)phenyl)-4-methylbenzamide

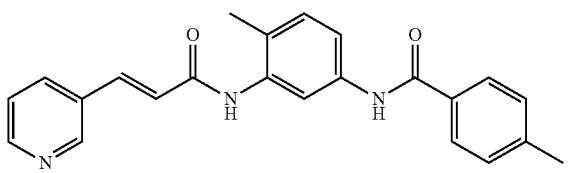 [SMILES: Cc1ccc(C(=O)Nc2ccc(C)c(NC(=O)/C=C/c3cccnc3)c2)cc1]

To a solution of the product of step 3 (0.25 g) and triethylamine (0.2 ml) in dichloromethane (25 ml), a solution of 4-methylbenzoyl chloride (0.5 g) in dichloromethane (10 ml) was added dropwise slowly in an ice-bath with the temperature no more than 5° C. After addition, the reaction was carried out for to 30 min in an ice-bath, and then at room temperature overnight. The completion of reaction was indicated by TLC. After that potassium carbonate solution (10%) was added, and then a solid was precipitated, and filtered out. The filter cake was washed with water, and recrystallized from ethyl acetate to give a solid.

$^1$HNMR (DMSO-d$_6$) (ppm): δ2.22 (s, 3-H), δ2.50 (s, 3H), δ7.09 (d, 1H), δ7.20 (d, 1H), δ7.49-7.64 (m, 3H), δ7.88 (d, 2H), δ8.05 (t, 2H), δ8.59 (d, 1H), δ8.83 (s, 1H), δ9.61 (s, 1H), δ10.18 (s, 1H).

Example 2

N-(4-methyl-3-(3-(pyridin-3-yl)acrylamido)phenyl)-4-fluoro benzamide (Compound 2)

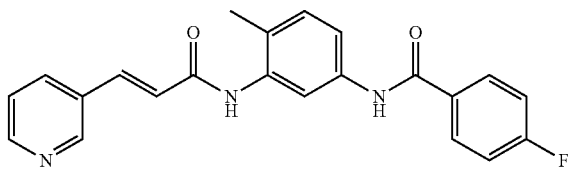 [SMILES: Cc1ccc(NC(=O)c2ccc(F)cc2)cc1NC(=O)/C=C/c1cccnc1]

The compound was synthesized by reference to example 1.
$^1$HNMR (DMSO-d$_6$) (ppm): δ2.23 (s, 3H), δ7.10 (d, 1H), δ7.21 (d, 1H), δ7.36 (t, 2H), δ7.49 (dd, 1H), δ7.55 (dd, 1H), δ7.62 (d, 1H), δ8.02-8.06 (m, 4H), δ8.59 (dd, 1H), δ8.83 (s, 1H), δ9.59 (s, 1H), δ10.26 (s, 1H).

Example 3

N-(4-methyl-3-(3-(pyridin-3-yl)acrylamido)phenyl)-2,4-difluoro benzamide (Compound 3)

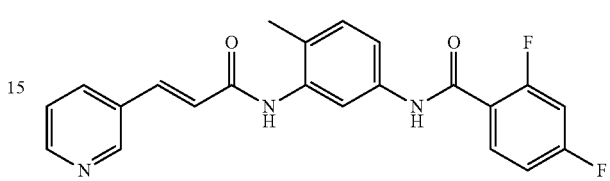

The compound was synthesized by reference to in example 1.
$^1$HNMR (DMSO-d$_6$) (ppm): δ2.23 (s, 3H), δ7.11 (d, 1H), δ7.20-7.25 (m, 2H), δ7.43-7.50 (m, 3H), δ7.62 (d, 1H), δ7.74 (q, 1H), δ7.97 (s, 1H), δ8.06 (d, 1H), δ8.59 (dd, 1H), δ8.83 (d, 1H), δ9.65 (s, 1H), δ10.45 (s, 1H).

Example 4

N-(4-methyl-3-(3-(pyridin-3-yl)acrylamido)phenyl)-2,4-dichloro benzamide (Compound 4)

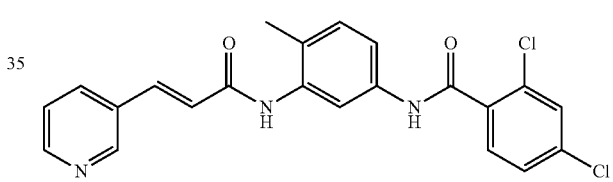

The compound was synthesized by reference to example 1.
$^1$HNMR (DMSO-d$_6$) (ppm): δ2.22 (s, 3H), δ7.10 (d, 1H), δ7.21 (d, 1H), δ7.46-7.49 (m, 2H), δ7.55 (dd, 1H), δ7.624 (t, 2H), δ7.77 (dd, 1H), δ7.97 (s, 1H), δ8.06 (d, 1H), δ8.59 (dd, 1H), δ8.83 (d, 1H), δ9.67 (s, 1H), δ10.57 (s, 1H).

Example 5

N-(4-methyl-3-(3-(pyridin-3-yl)acrylamido)phenyl)-3,5-bis-(trifluoromethyl)benzamide (Compound 5)

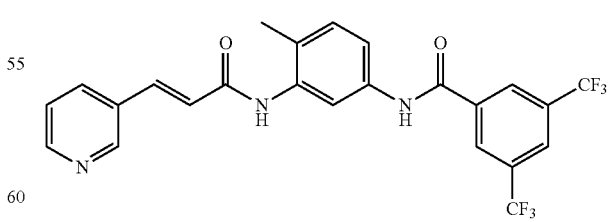

The compound was synthesized by reference to example 1.
$^1$HNMR (DMSO-d$_6$) (ppm): δ2.23 (s, 3H), δ7.13 (d, 1H), δ7.49 (dd, 1H), δ7.55 (dd, 1H), δ7.62 (d, 1H), δ7.98 (s, 1H), δ8.06 (d, 1H), δ8.30 (s, 1H), δ8.59 (dd, 2H), δ8.63 (s, 1H), δ8.84 (d, 1H), δ9.63 (s, 1H), δ10.67 (s, 1H).

Example 6

N-(4-methyl-3-(3-(pyridin-3-yl)acrylamido)phenyl)-3-(trifluoromethyl)benzamide (Compound 6)

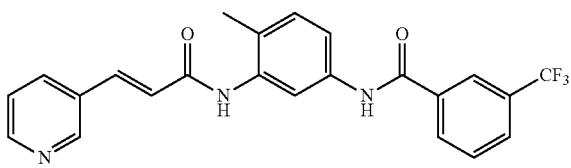 [SMILES: Cc1ccc(NC(=O)c2cccc(C(F)(F)F)c2)cc1NC(=O)/C=C/c1cccnc1]

The compound was synthesized by reference to example 1.
¹HNMR (DMSO-d₆) (ppm): δ2.24 (s, 3H), δ7.11 (d, 1H), δ7.23 (d, 1H), δ7.49 (dd, 1H), δ7.58 (dd, 1H), δ7.78 (t, 1H), δ7.97 (d, 1H), δ8.06 (d, 2H), δ8.28 (t, 2H), δ8.58 (dd, 1H), δ9.62 (s, 1H), δ10.50 (s, 1H).

Example 7

N-(4-methyl-3-(3-(pyridin-3-yl)acrylamido)phenyl)-3-(rifluoromethyl)-4-methyl benzamide (Compound 7)

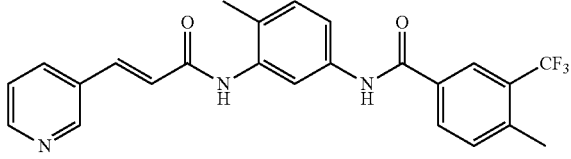 [SMILES: Cc1ccc(NC(=O)c2ccc(C)c(C(F)(F)F)c2)cc1NC(=O)/C=C/c1cccnc1]

The compound was synthesized by reference to example 1.
¹HNMR (DMSO-d₆) (ppm): δ2.23 (s, 3H), δ2.50 (s, 3H), δ7.11 (d, 1H), δ7.22 (d, 1H), δ7.50 (dd, 1H), δ7.57 (dd, 1H), δ7.64 (t, 1H), δ8.05 (t, 2H), δ8.16 (d, 1H), δ8.25 (s, 1H), δ8.59 (dd, 1H), δ8.84 (d, 1H), δ9.61 (s, 1H), δ10.43 (s, 1H).

Example 8

N-(4-methyl-3-(3-(pyridin-3-yl)acrylamido)phenyl)-3-chloro-4-methyl benzamide (Compound 8)

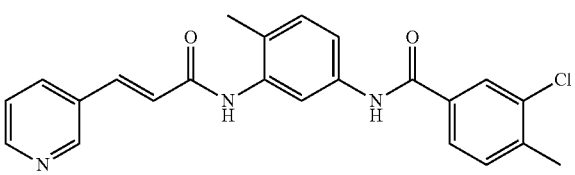 [SMILES: Cc1ccc(C(=O)Nc2ccc(C)c(NC(=O)/C=C/c3cccnc3)c2)cc1Cl]

The compound was synthesized by reference to example 1.
¹HNMR (DMSO-d₆) (ppm): δ2.23 (s, 3H), δ2.41 (s, 3H), δ7.10 (d, 1H), δ7.21 (d, 1H), δ7.47-7.51 (m, 3H), δ7.63 (d, 1H), δ7.86 (dd, 1H), δ8.03-8.07 (m, 3H), δ8.58 (dd, 1H), δ8.84 (s, 1H), δ9.61 (s, 1H), δ10.30 (s, 1H).

Example 9

N-(4-methyl-3-(3-(pyridin-3-yl)acrylamido)phenyl)-4-fluoro-3-(trifluoromethyl)benzamide (Compound 9)

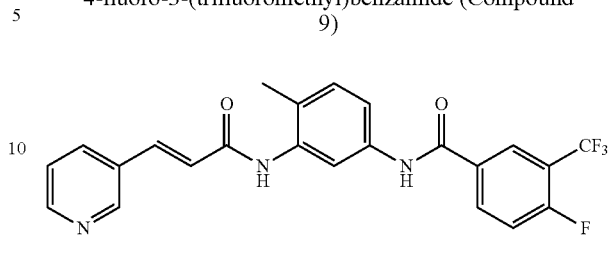

The compound was synthesized by reference to example 1.
¹HNMR (DMSO-d₆) (ppm): δ2.223 (s, 3H), δ7.08 (d, 1H), δ7.21 (d, 1H), δ7.42-7.49 (m, 2H), δ7.60-7.70 (m, 2H), δ7.77-7.81 (m, 2H), δ7.94 (s, 1H), δ8.05 (d, 1H), δ8.58 (dd, 1H), δ8.82 (d, 1H), δ9.60 (s, 1H), δ10.55 (s, 1H).

Example 10

N-(4-methyl-3-(3-(pyridin-3-yl)acrylamido)phenyl)-3-fluoro-5-(trifluoromethyl)benzamide (Compound 10)

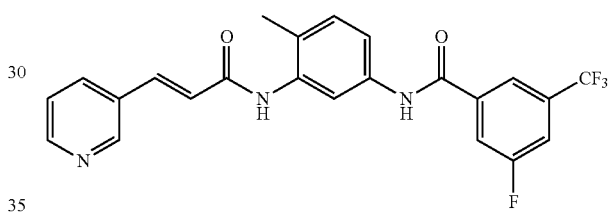

The compound was synthesized by reference to example 1.
¹HNMR (DMSO-d₆) (ppm): δ2.23 (s, 3H), δ7.12 (d, 1H), δ7.19 (d, 1H), δ7.49 (dd, 1H), δ7.54 (dd, 1H), δ7.62 (d, 1H), δ7.89-8.19 (m, 5H), δ8.58 (dd, 1H), δ8.34 (d, 1H), δ9.65 (s, 1H), δ10.55 (s, 1H).

Example 11

N-(4-methyl-3-(3-(pyridin-3-yl)acrylamido)phenyl)-4-((4-methyl piperazin-1-yl)methyl)benzamide (Compound 11)

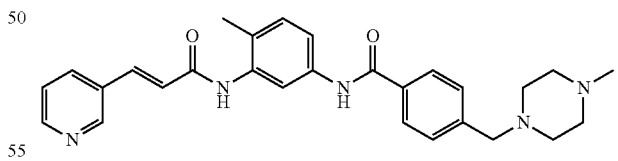

N-(3-(3-(pyridin-3-yl)acrylamido)phenyl)-4-(chloromethyl)benzamide was synthesized by reference to example 1. To N-(3-(3-(pyridin-3-yl)acrylamido)phenyl)-4-(chloromethyl)benzamide (0.4 g) and triethylamine (1.0 ml) in anhydrous DMF (20 ml), N-methyl piperazine (0.5 ml) was added dropwise slowly in an ice-bath. After addition, the reaction was carried out for 2 h in an ice-bath, and then at room temperature overnight. The completion of reaction was indicated by TLC. The mixture was concentrated under reduced pressure. The residue was purified on silica gel column using CHCl₃/CH₃OH (1:1) as an eluent. Then concentration of the eluent and crystallization provided a white solid.

¹HNMR (DMSO-d₆) (ppm): δ2.23 (s, 3H), δ2.24 (t, 4H), δ2.50 (m, 7H), δ3.53 (s, 2H), δ7.09 (d, 1H), δ7.20 (d, 1H), δ7.42-7.64 (m, 5H), δ7.91 (d, 2H), δ8.04 (t, 2H), δ8.58 (dd, 1H), δ8.83 (d, 1H), δ9.58 (s, 1H), δ10.20 (s, 1H).

Example 12

N-(4-methyl-3-(3-pyridin-3-yl)acryl)acrylamido)phenyl)-4-((cis-3,5-dimethylpiperazin-1-yl)methyl)benzamide (Compound 12)

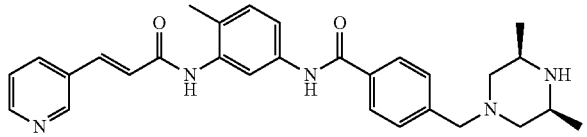 [SMILES: Cc1ccc(NC(=O)c2ccc(CN3C[C@@H](C)N[C@@H](C)C3)cc2)cc1NC(=O)/C=C/c1cccnc1]

The compound was synthesized by reference to example 11.

¹HNMR (DMSO-d₆) (ppm): δ0.88-0.89 (d, 6H), δ1.50 (t, 2H), δ2.22 (s, 3H), δ2.6 (m, 4H), δ3.38 (m, 3H), δ7.09 (d, 1H), δ7.20 (d, 1H), δ7.41-7.56 (m, 4H), δ7.62 (d, 1H), δ7.90 (d, 2H), δ8.04 (t, 2H), δ8.59 (dd, 1H), δ8.83 (d, 1H), δ9.58 (s, 1H), δ10.20 (s, 1H).

Example 13

N-(4-methyl-3-(3-(pyridin-3-yl)acrylamido)phenyl)-4-((4-ethylpiperazin-1-yl)methyl)benzamide (compound 13)

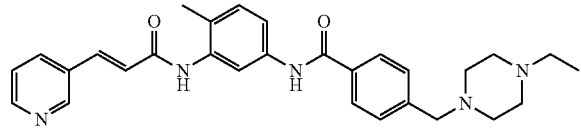 [SMILES: CCN1CCN(Cc2ccc(C(=O)Nc3ccc(C)c(NC(=O)/C=C/c4cccnc4)c3)cc2)CC1]

The compound was synthesized by reference to example 11.

¹HNMR (DMSO-d₆) (ppm): δ0.97 (t, 3H), δ1.20 (q, 2H), δ2.23-2.50 (m, 1H), δ3.52 (s, 2H), δ7.10 (d, 1H), δ7.20 (d, 1H), δ7.42-7.56 (m, 4H), δ7.62 (d, 1H), δ7.91 (d, 2H), δ8.04 (t, 2H), δ8.59 (dd, 1H), 8.83 (d, 1H), δ9.59 (s, 1H), δ10.15 (s, 1H).

Example 14

N-(4-methyl-3-(3-(pyridin-3-yl)acrylamido)phenyl)-4-((piperidin-1-yl)methyl)benzamide (Compound 14)

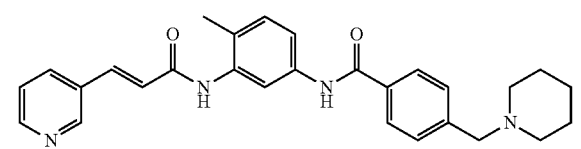 [SMILES: Cc1ccc(NC(=O)c2ccc(CN3CCCCC3)cc2)cc1NC(=O)/C=C/c1cccnc1]

The compound was synthesized by reference to example 11.

¹HNMR (DMSO-d₆) (ppm): δ1.40-1.51 (m, 1H), δ2.22-2.51 (m, 7H), δ3.49 (s, 2H), δ7.10 (d, 1H), δ7.20 (d, 1H), δ7.42-7.64 (m, 5H), δ7.90 (d, 1H), δ8.05 (t, 3H), δ8.59 (dd, 1H), δ8.84 (d, 1H), δ9.62 (s, 1H), δ10.22 (s, 1H).

Example 15

N-(4-methyl-3-(3-(pyridin-3-yl)acrylamido)phenyl)-4-(morpholin-4-ylmethyl)benzamide (Compound 15)

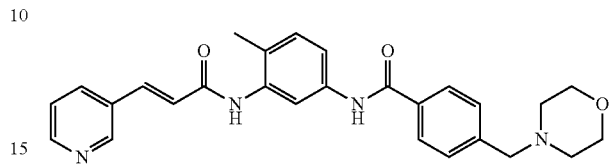

The compound was synthesized by reference to example 11.

¹HNMR (DMSO-d₆) (ppm): δ2.22 (s, 3H), δ2.41 (t, 4H), δ3.54-3.59 (m, 6H), δ7.09 (d, 1H), δ7.20 (d, 1H), δ7.44-7.56 (m, 4H), δ7.62 (d, 1H), δ7.92 (d, 2H), δ8.04 (t, 2H), δ8.58 (dd, 1H), 8.83 (d, 1H), δ9.58 (s, 1H), δ10.20 (s, 1H).

Example 16

N-(4-methyl-3-(3-(pyridin-3-yl)acrylamido)phenyl)-4-((4-methyl-1,4-homopiperazin-1-yl)methyl)benzamide (Compound 16)

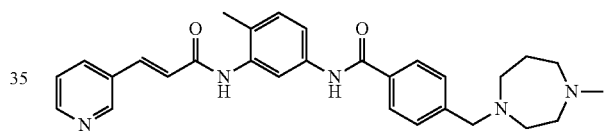

The compound was synthesized by reference to example 11.

¹HNMR (DMSO-d₆) (ppm): δ1.70-1.73 (m, 1H), δ2.23-2.25 (d, 1H), δ2.49-2.67 (m, 8H), δ3.67 (s, 2H), δ7.07-7.21 (q, 2H), δ7.44-7.64 (m, 5H), δ7.89-8.06 (m, 4H), δ8.58-8.59 (dd, 1H), δ8.83-8.83 (d, 1H), δ9.58 (s, 1H), δ10.19 (s, 1H).

Example 17

N-(4-methyl-3-(3-(pyridin-3-yl)acrylamido)phenyl)-4-((diethylamino)methyl)benzamide (Compound 17)

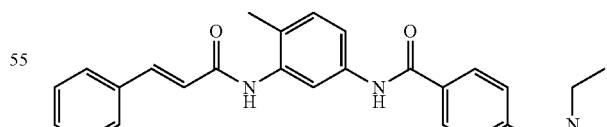

The compound was synthesized by reference to example 11.

¹HNMR (DMSO-d₆) (ppm): δ1.25 (t, 6H), δ2.24 (s, 3H), δ3.08 (m, 4H), δ4.39 (s, 2H), δ7.12 (d, 1H), δ7.22 (d, 1H), δ7.48-7.74 (m, 1H), δ8.06 (d, 3H), δ8.59 (dd, 1H), δ8.83 (d, 1H), δ9.63 (s, 1H), δ10.00 (s, 1H), δ10.36 (s, 1H).

Example 18

N-(4-methyl-3-(3-(pyridin-3-yl)acrylamido)phenyl)-4-((4-(2-hydroxyethyl)piperazin-1-yl)methyl)benzamide (Compound 18)

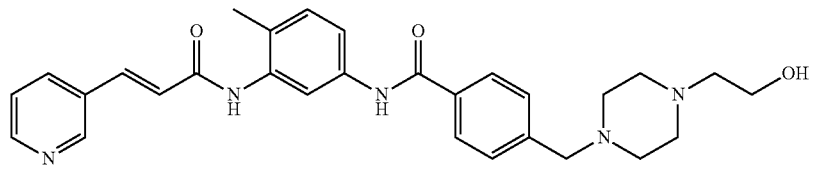 [SMILES: Cc1ccc(NC(=O)c2ccc(CN3CCN(CCO)CC3)cc2)cc1NC(=O)/C=C/c1cccnc1]

The compound was synthesized by reference to example 11.

$^1$HNMR (DMSO-d$_6$) (ppm): δ2.22 (s, 3H), δ2.35-2.50 (m, 10H), δ3.33-3.52 (m, 4H), δ7.10 (d, 1H), δ7.20 (d, 1H), δ7.42-7.56 (m, 5H), δ7.62 (d, 1H), δ7.91 (d, 2H), δ8.04 (t, 2H), δ8.58 (d, 1H), δ8.83 (s, 1H), δ9.62 (s, 1H), δ10.19 (s, 1H).

Example 19

N-(4-methyl-3-(3-(pyridin-3-yl)acrylamido)phenyl)-4-((4-methylpiperazin-1-yl)methyl)-3-(trifluoromethyl)benzamide (Compound 19)

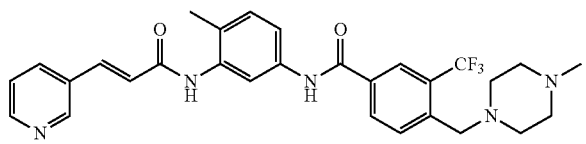

Step 1. Synthesis of 4-(bromomethyl)-3-(trifluoromethyl)benzoic acid 1.0 g of 4-methyl-3-(trifluoromethyl)benzoic acid was dissolved in isopropyl acetate (q.s.). To the mixture, sodium bromate aqueous solution (10 ml, containing 2.2 g of sodium bromate) and sodium bisulfite aqueous solution (10 ml, containing 1.52 g of sodium bisulfite) were added alternatively with stirring. After addition, the solution became brownish red. The mixture was heated to reflux until the solution became colorless. Then the organic layer was separated. Again, to the mixture, sodium bromate aqueous solution (10 ml, containing 2.2 g sodium bromate) and sodium bisulfite aqueous solution (10 ml, containing 1.52 g sodium bisulfite) were added alternatively and the mixture was heated to reflux until the solution became colorless. Then the organic layer was separated. Continually, to the mixture, a sodium bromate aqueous solution (10 ml, containing 2.2 g sodium bromate) and a sodium bisulfite aqueous solution (10 ml, containing 1.52 g sodium bisulfite) were added alternatively, and the mixture was heated to reflux until the solution became colorless. Then the organic layer was separated. The organic layer was washed with 5% sodium sulfate solution twice and 15% sodium chloride solution twice, dried over anhydrous Na$_2$SO$_4$, filtered, concentrated under reduced pressure to dry.

The is residue was stirred in petroleum ether, and filtered to give a white solid. m.p. 140-145° C.

Step 2. Synthesis of 4-(bromomethyl)-3-(trifluoromethyl)benzoyl chloride

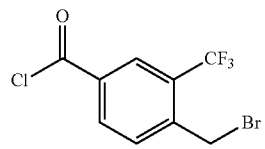 [SMILES: O=C(Cl)c1ccc(CBr)c(C(F)(F)F)c1]

1.00 g of 4-(bromomethyl)-3-(trifluoromethyl)benzoic acid was dissolved in dichloromethane (q.s.), then 2 drops of anhydrous N,N'-dimethylformamide were added. Then 2 ml of oxalyl chloride was added dropwise to the mixture. The reaction mixture was reacted at room temperature for 5 h, and concentrated to provide the product.

Step 3. Synthesis of N-(4-methyl-3-(3-(pyridin-3-yl)acrylamido)phenyl)-4-(bromomethyl-3-trifluoromethyl)benzamide

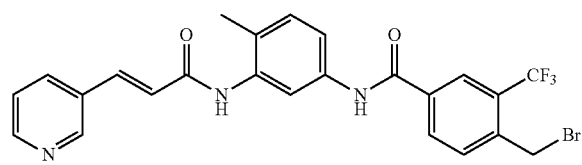 [SMILES: Cc1ccc(NC(=O)c2ccc(CBr)c(C(F)(F)F)c2)cc1NC(=O)/C=C/c1cccnc1]

To a solution of N-(5-amino-2-methylphenyl)-3-pyridinyl acrylamide (0.45 g) and triethylamine (0.4 ml) in dichloromethane (20 ml), a solution of 4-(bromomethyl)-3-(trifluoromethyl)benzoyl chloride in dichloromethane (10 ml) was added dropwise in an ice-bath with the temperature no more than 5° C. After addition, the ice-bath was removed. The reaction was carried out at room temperature for 5 h. The completion of reaction was indicated by TLC. Potassium carbonate aqueous solution (10%) was added to the mixture. The organic layer was separated, dried over anhydrous Na$_2$SO$_4$, filtered, and concentrated under reduced pressure. The residue was purified on silica gel column using EtOAc as an eluent. The eluent was collected, concentrated to dry and crystallized.

Step 4. Synthesis of N-(4-methyl-3-(3-(pyridin-3-yl)acrylamido)phenyl)-4-((4-methylpiperazin-1-yl)methyl)-3-(trifluoromethyl)benzamide 0.4 g of N-(4-methyl-3-(3-(pyridin-3-yl)acrylamido)phenyl)-4-(bromomethyl)-3-(trifluoromethyl)benzamide was added into 20 ml anhydrous tetrahydrofuran, and then 1.0 g of potassium carbonate and 1.0 ml of 4-methyl piperazine. The reaction mixture was heated to reflux for 10 h. The completion of reaction was indicated by TLC. The reaction mixture was filtered, and the filtrate was evaporated to dry. 10 ml of water was added to dissolve the redundant 4-methylpiperazine and corresponding salts. The mixture was filtered, the filter cake was purified on silica gel column using ethyl acetate as an eluent to elute impurities, then using methanol as an eluent to elute the product. Concentration of the eluent under reduced pressure and crystallization gave a white solid.

$^1$HNMR (DMSO-d$_6$) (ppm): δ2.16 (s, 3H), δ2.23 (s, 3H), δ2.42-2.50 (m, 8H), δ3.68 (s, 2H), δ7.11 (d, 1H), δ7.22 (d, 1H), δ7.50 (dd, 1H), δ7.57 (dd, 1H), δ7.62 (d, 1H), δ7.92 (d, 1H) δ8.05 (t, 2H), δ8.22 (t, 2H), δ8.59 (dd, 1H), δ8.84 (d, 1H), δ9.62 (s, 1H), δ10.46 (s, 1H).

Example 20

N-(4-methyl-3-(3-(pyridin-3-yl)acrylamido)phenyl)-4-((4-ethylpiperazin-1-yl)methyl)-3-(trifluoromethyl)benzamide (Compound 20)

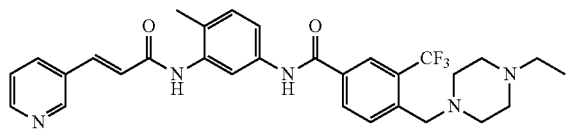

The compound was synthesized by reference to example 19.

$^1$HNMR (DMSO-d$_6$) (ppm): δ0.98 (t, 3H), δ2.24 (s, 3H), δ2.29-2.50 (m, 10H), δ3.68 (s, 2H), δ7.10 (d, 1H), δ7.23 (d, 1H), δ7.49 (dd, 1H), δ7.56 (dd, 1H), δ7.62 (d, 1H), δ7.92 (d, 1H), δ8.04 (t, 2H), δ8.23 (t, 2H), δ8.59 (dd, 1H), δ8.83 (d, 1H), δ9.58 (s, 1H), δ10.44 (s, 1H).

Example 21

N-(4-methyl-3-(3-(pyridin-3-yl)acrylamido)phenyl)-4-(morpholin-4-ylmethyl)-3-(trifluoromethyl)benzamide (Compound 21)

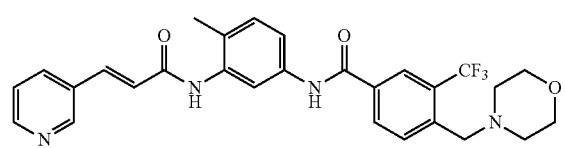 [SMILES: Cc1ccc(NC(=O)c2ccc(CN3CCOCC3)c(C(F)(F)F)c2)cc1NC(=O)/C=C/c1cccnc1]

The compound was synthesized by reference to example 19.

$^1$HNMR (DMSO-d$_6$) (ppm): δ2.24 (s, 3H), δ2.42 (t, 4H), δ3.61-3.69 (m, 6H), δ7.10 (d, 1H), δ7.22 (d, 1H), δ7.47-7.57 (m, 2H), δ7.62 (d, 1H), δ7.95 (d, 1H), δ8.04 (t, 2H), δ8.24 (t, 2H), δ8.59 (d, 1H), δ8.83 (s, 1H), δ9.58 (s, 1H), δ10.44 (s, 1H).

Example 22

N-(4-methyl-3-(3-(pyridin-3-yl)acrylamido)phenyl)-4-(((R)-3-(dimethylamino)pyrrolidin-1-yl)methyl)-3-(trifluoromethyl)benzamide (Compound 22)

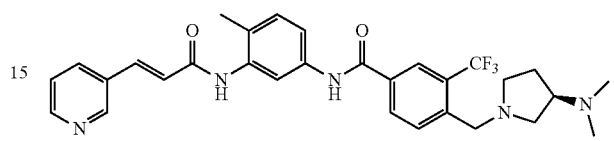

The compound was synthesized by reference to example 19.

$^1$HNMR (DMSO-d$_6$) (ppm): δ1.52 (s, 6H), δ1.64-1.65 (m, 1H), δ2.08 (m, 1H), δ2.23 (s, 3H), δ2.37 (m, 1H), δ2.61-2.69 (m, 4H), δ3.80 (q, 2H), δ7.20-7.25 (m, 2H), δ7.49 (dd, 1H) 67.57 (d, 1H), 7.61 (d, 1H), δ7.89 (d, 1H), δ8.01 (s, 1H), δ8.09 (d, 1H), δ8.26 (d, 2H), δ8.57 (dd, 1H), δ8.84 (d, 1H), δ9.97 (s, 1H), δ10.60 (s, 1H).

Example 23

N-(4-methyl-3-(3-(pyridin-3-yl)acrylamido)phenyl)-4-(((S)-3-(dimethylamino)pyrrolidin-1-yl)methyl)-3-(trifluoromethyl)benzamide (Compound 23)

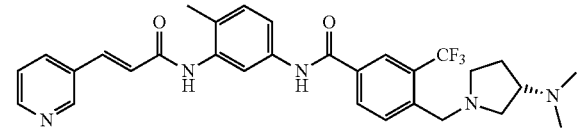

The compound was synthesized by reference to example 19.

$^1$HNMR (DMSO-d$_6$) (ppm): δ1.64-1.65 (m, 1H), δ1.87-1.89 (m, 1H), δ2.08 (s, 6H), δ2.23 (s, 3H), δ2.32-2.40 (m, 1H), δ2.61-2.74 (m, 4H), δ3.77 (q, 2H), δ7.12 (d, 1H), δ7.22 (d, 1H), δ7.49 (dd, 1H), δ7.57 (dd, 1H), δ7.62 (d, 1H), δ7.89 (d, 1H), δ8.02-8.07 (m, 2H), δ8.23 (d, 2H), δ8.58 (dd, 1H), δ8.83 (d, 1H), δ9.63 (s, 1H), δ10.45 (s, 1H).

Example 24

N-(4-methyl-3-(3-(pyridin-3-yl)acrylamido)phenyl)-4-((3-(dimethylamino)pyrrolidin-1-yl)methyl)-3-(trifluoromethyl)benzamide (Compound 24)

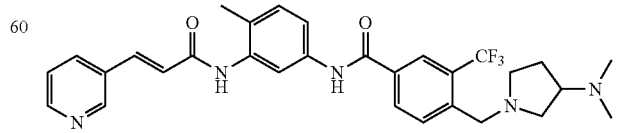

The compound was synthesized by reference to example 19.

¹HNMR (DMSO-d₆) (ppm): δ1.64-1.65 (m, 1H), δ1.87-1.89 (m, 1H), δ2.07-2.09 (d, 6H), δ2.22 (s, 3H), δ2.31-2.41 (m, 1H), δ2.62-2.74 (m, 4H), δ3.73-3.84 (q, 2H), δ7.00-7.22 (q, 2H), δ7.48-7.64 (m, 3H), δ7.89-8.07 (m, 3H), δ8.22-8.24 (d, 2H), δ8.57-8.59 (dd, 1H), δ8.83-8.84 (d, 1H), δ9.63 (s, 1H), δ10.45 (s, 1H).

Example 25

N-(4-methyl-3-(3-(pyridin-3-yl)acrylamido)phenyl)-4-((4-methyl-1,4-homopiperazin-1-yl)methyl)-3-(trifluoromethyl)benzamide (Compound 25)

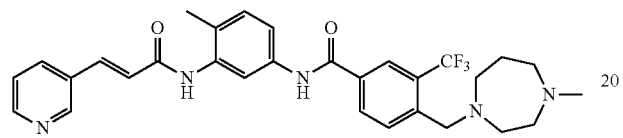

The compound was synthesized by reference to example 19.

MS (FAB): 552 (M+1)

Example 26

N-(4-methyl-3-(3-(pyridin-3-yl)acrylamido)phenyl)-4-((4-dimethyl piperazin-1-yl)methyl)-3-bromobenzamide (Compound 26)

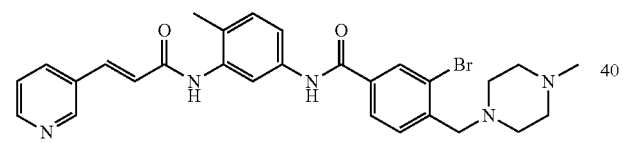

The compound was synthesized by reference to example 19.

MS (FAB): 549 (M+1)

Example 27

N-(4-methyl-3-(3-pyridin-3-yl)acrylamido)phenyl)-4-((cis-3,5-dimethylpiperazin-1-yl)methyl)-3-bromobenzamide (Compound 27)

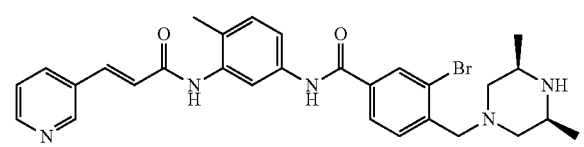 [SMILES: Cc1ccc(NC(=O)c2ccc(CN3C[C@@H](C)N[C@@H](C)C3)c(Br)c2)cc1NC(=O)/C=C/c1cccnc1]

The compound was synthesized by reference to example 19.

MS (FAB): 563 (M+1)

Example 28

N-(4-methyl-3-(3-(pyridin-3-yl)acrylamido)phenyl)-4-((4-ethylpiperazin-1-yl)methyl)-3-bromobenzamide (Compound 28)

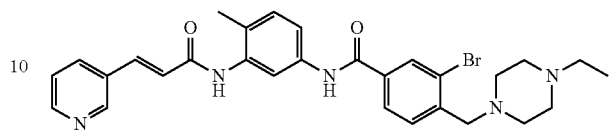

The compound was synthesized by reference to example 19.

MS (FAB): 563 (M+1)

Example 29

N-(4-methyl-3-(3-(pyridin-3-yl)acrylamido)phenyl)-4-(morpholin-4-ylmethyl)-3-bromobenzamide (Compound 29)

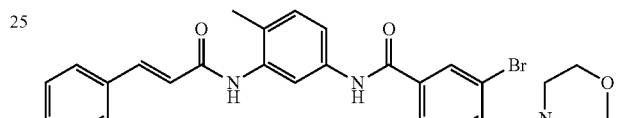

The compound was synthesized by reference to example 19.

MS (FAB): 536 (M+1)

Example 30

N-(4-methyl-3-(3-(pyridin-3-yl)acrylamido)phenyl)-4-((4-methyl-1,4-homopiperazin-1-yl)methyl)-3-bromobenzamide (Compound 30)

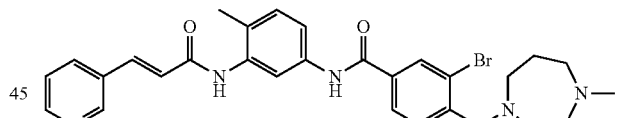

The compound was synthesized by reference to example 19.

MS (FAB): 563 (M+1)

Example 31

N-(4-methyl-3-(3-(pyrimidin-5-yl)acrylamido)phenyl)-3,5-bis-(trifluoromethyl)benzamide (Compound 31)

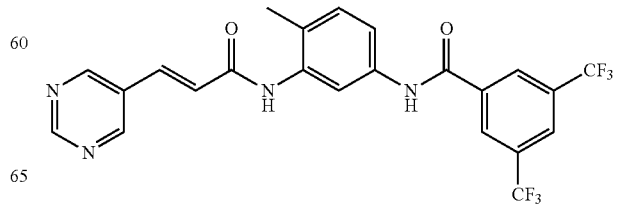

Step 1. Synthesis of n-buthyl 3-pyrimidin-5-acrylate

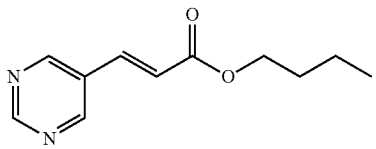

A dried reaction bottle was charged with 0.237 g of triphenylphosphine and 0.099 g of palladium acetate. After that 10 ml of anhydrous N,N'-dimethylformamide was added to dissolve the mixture with stirring, and then 3 ml of triethylamine was added dropwise to the solution. The mixture was reacted at 80° C. for 10 min under the protection of $N_2$. Once the solution became deep red, 1.5 g of 5-bromopyrimidine and 2.7 ml of n-butyl acrylate was added. Then, the reaction mixture was heated to 150° C., and reacted for 6 h. The completion of reaction was indicated by TLC. The reaction solution was cooled, filtered, and the filter cake was rinsed with EtOAc. The filtrate was washed with water and saturated sodium chloride solution. The organic layer was dried over anhydrous $Na_2SO_4$, filtered, and concentrated under reduced pressure. The residue was purified on silica gel column using EtOAc/petroleum ether/Ethanol (1:4) as eluent. The eluent was concentrated and cooled to crystallize to give a solid.

Step 2. Synthesis of 3-pyrimidin-5-acrylic acid

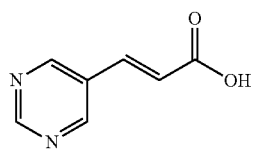 [SMILES: O=C(O)/C=C/c1cncnc1]

1.0 g of the product of step 1 was dissolved in a solution of methanol, tetrahydrofuran and water (30 nm, 1:1:1) with stirring, then 0.40 g lithium hydroxide was added. The reaction mixture was stirred at room temperature for 4 h. The completion of reaction was indicated by TLC. The reaction solution was acidified with dilute hydrochloric acid to adjust PH to 5-6 to precipitate solid. The mixture was cooled, left to stand, filtered, and dried to give a gray solid.

Step 3. Synthesis of 3-pyrimidin-5-ylacryloyl chloride hydrochloride

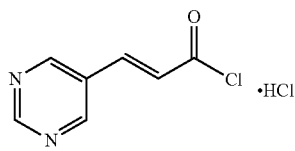 [SMILES: O=C(Cl)/C=C/c1cncnc1 ; Cl]

1.5 g of the product of step 2 was added to 20 ml dichloromethane, then 3 drops of N,N-dimethylformamide was added. 2.7 ml of oxalyl chloride was added dropwise to the mixture at room temperature. After addition, the reaction mixture was reacted overnight at room temperature. Then the reaction mixture was concentrated under reduced pressure to give a grey solid.

Step 4. Synthesis of N-(2-methyl-5-nitrophenyl)-3-(pyrimidin-5-yl)acrylamide

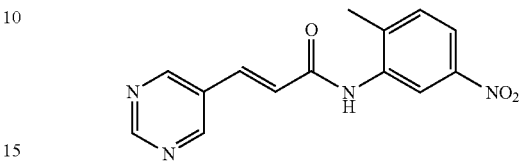

To a suspension of the product of step 3 (2.05 g) in anhydrous dichloromethane (30 ml), a solution of 2-methyl-5-nitroaniline (3.04 g) and triethylamine (8 ml, excess allowed) in dichloromethane (15 ml) was added dropwise slowly in an ice-bath with the temperature no more than 5° C. After addition, the reaction was carried out for 30 min in an ice-bath, and then at room to temperature for 3 h. Completion of reaction was indicated by TLC. Potassium carbonate solution (10%) was added to the mixture. Then the mixture was extracted with EtOAc (20 ml*3). The organic layer was dried over anhydrous $Na_2SO_4$, filtered, and concentrated under reduced pressure to recover the solvent. The residue was purified on silica gel column (EtOAc/petroleum ether 4:1). The eluent was collected, concentrated under reduced pressure to give a yellow powdered solid.

Step 5. Synthesis of N-(5-amino-2-methylphenyl)-3-(pyrimidin-5-yl)acrylamide

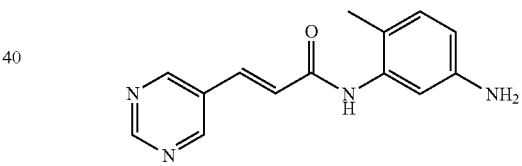

1.42 g of the product of step 4 was added to a mixture of ethanol (90 ml) and water (30 ml), and then 2.24 g of iron powder and 0.80 g of ammonium chloride were added. After addition, the solution was heated to 70° C. and reacted for 30 min. The completion of reaction was indicated by TLC. The reaction mixture was filtered. The filter cake was washed with hot ethanol repeatedly. The filtrate was concentrated under reduced pressure to give a yellow solid. Then 20 ml of potassium carbonate solution (10%) was added to the solid. The mixture was stirred, left to stand, filtered, and dried to give a solid.

Step 6. Synthesis of N-(4-methyl-3-(3-(pyrimidin-5-yl)acrylamido)phenyl)-3,5-bis-(trifluoromethyl)benzamide To a solution of the product of step 5 (0.254 g) and triethylamine (0.2 ml) in dichloromethane (15 ml), a solution of 3,4-di-(trifluoromethyl)benzoyl chloride (0.30 g) in dichloromethane (10 ml) was added dropwise slowly in an ice-bath to with the temperature no more than 5° C. After addition, the reaction was carried out for 30 min, and then at room temperature overnight. The completion of reaction was indicated by TLC. Then potassium carbonate solution (10%) was added. The mixture was extracted with EtOAc (20 ml*3). The organic layer was dried over anhydrous $Na_2SO_4$, filtered, and concentrated under reduced pressure to recover the solvent. The residue was purified on silica gel column (EtOAc/petroleum ether 2:1). The eluent was collected and concentrated under reduced pressure to give a yellow powdered solid.

$^1$HNMR (DMSO-$d_6$) (ppm): δ2.26 (s, 3H), δ7.21 (d, 2H), δ7.27 (d, 1H), δ7.59-7.64 (m, 2H), δ8.05 (s, 1H), δ8.39 (s, 1H), δ8.62 (s, 2H), δ9.09 (s, 2H), δ9.19 (s, 1H), δ9.69 (s, 1H), δ10.69 (s, 1H).

Example 32

N-(4-methyl-3-(3-(pyrimidin-5-yl)acrylamido)phenyl)-4-methyl-3-(trifluoromethyl)benzamide (Compound 32)

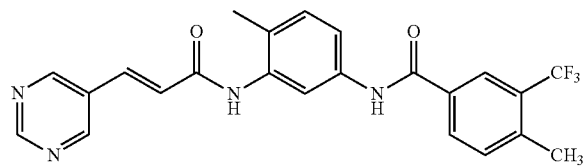 [SMILES: Cc1ccc(NC(=O)c2ccc(C)c(C(F)(F)F)c2)cc1NC(=O)/C=C/c1cncnc1]

The compound was synthesized by reference to example 31.

$^1$HNMR (DMSO-$d_6$) (ppm): δ2.23 (s, 3H), δ2.50 (s, 3H), δ7.23 (m, 2H), δ7.61 (m, 3H), δ8.00 (s, 1H), δ8.16 (d, 1H), δ8.25 (s, 1H), δ9.09 (s, 2H), δ9.18 (s, 1H), δ10.03 (s, 1H).

Example 33

N-(4-methyl-3-(3-(pyrimidin-5-yl)acrylamido)phenyl)-5-fluoro-3-(trifluoromethyl)benzamide (Compound 33)

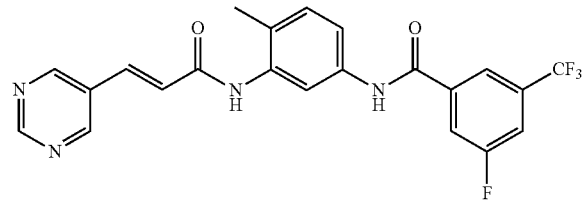 [SMILES: Cc1ccc(NC(=O)c2cc(F)cc(C(F)(F)F)c2)cc1NC(=O)/C=C/c1cncnc1]

The compound was synthesized by reference to example 31.

$^1$HNMR (DMSO-$d_6$) (ppm): δ2.25 (s, 3H), δ7.20 (d, 1H), δ7.25 (d, 1H), δ7.58 (dd, 1H), δ7.63 (s, 1H), δ7.96 (d, 1H), δ8.04 (s, 1H), δ8.14 (t, 2H), δ9.08 (s, 2H), δ9.18 (s, 1H), δ9.66 (s, 1H), δ10.51 (s, 1H).

Example 34

N-(4-methyl-3-(3-(pyrimidin-5-yl)acrylamido)phenyl)-4-methyl benzamide (Compound 34)

The compound was synthesized by reference to example 31.

MS (FAB): 373 (M+H).

Example 35

N-(4-methyl-3-(3-(pyrimidin-5-yl)acrylamido)phenyl)-4-fluorobenzamide (Compound 35)

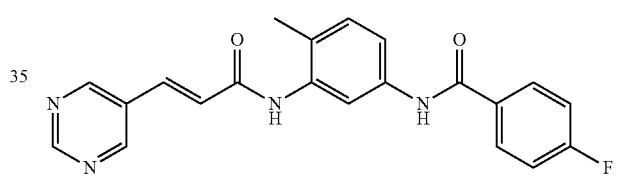

The compound was synthesized by reference to example 31.

MS (FAB): 377 (M+1).

Example 36

N-(4-methyl-3-(3-(pyrimidin-5-yl)acrylamido)phenyl)-2,4-difluorobenzamide (Compound 36)

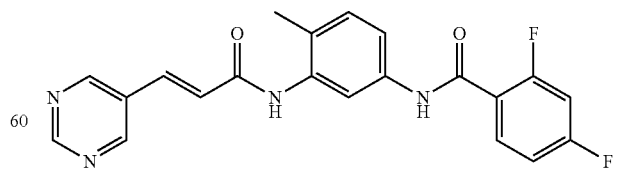

The compound was synthesized by reference to example 31.

MS (FAB): 395 (M+1).

Example 37

N-(4-methyl-3-(3-(pyrimidin-5-yl)acrylamido)phenyl)-2,4-dichlorobenzamide (Compound 37)

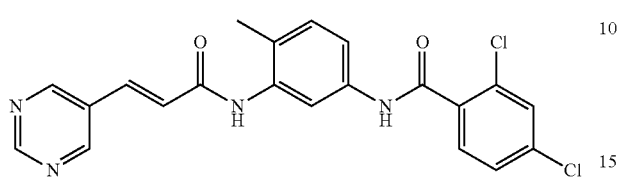

The compound was synthesized by reference to example 31.

MS (FAB): 427 (M+1).

Example 38

N-(4-methyl-3-(3-(pyrimidin-5-yl)acrylamido)phenyl)-4-((4-methylpiperazin-1-yl)methyl)benzamide (Compound 38)

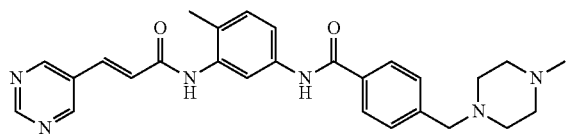

The compound was synthesized by reference to example 31.

MS (FAB): 471 (M+1).

Example 39

N-(4-methyl-3-(3-(pyrimidin-5-yl)acrylamido)phenyl)-4-((4-methylpiperazin-1-yl)methyl)-3-(trifluoromethyl)benzamide (Compound 39)

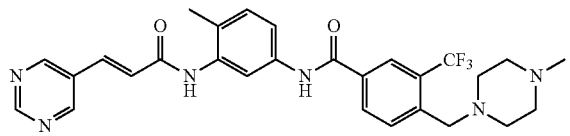

The compound was synthesized by reference to example 31.

$^1$HNMR (DMSO-$d_6$) (ppm): δ 2.24 (s, 3H), δ 2.71 (s, 3H), δ 3.76 (s, 2H), δ 7.23 (m, 2H), δ 7.57-7.63 (m, 2H), δ 7.92 (d, 1-H), δ 8.03 (s, 1H), δ 8.26 (d, 1H), δ 8.29 (s, 1H), δ 9.09 (s, 2H), δ 9.18 (s, 1H), δ 9.70 (s, 1H) δ 10.48 (s, 1H).

Example 40

N-(4-methyl-3-(3-(pyrimidin-5-yl)acrylamido)phenyl)-4-((4-ethylpiperazin-1-yl)methyl)-3-(trifluoromethyl)benzamide (Compound 40)

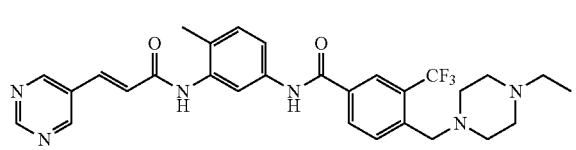 [SMILES: CCN1CCN(Cc2ccc(C(=O)Nc3ccc(C)c(NC(=O)/C=C/c4cncnc4)c3)cc2C(F)(F)F)CC1]

The compound was synthesized by reference to example 31.

MS (FAB): 553 (M+1).

Example 41

N-(4-methyl-3-(3-(pyrimidin-5-yl)acrylamido)phenyl)-4-s (morpholin-4-ylmethyl)-3-(trifluoromethyl)benzamide (Compound 41)

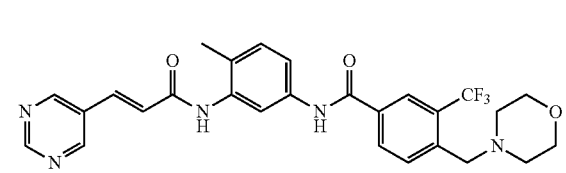 [SMILES: Cc1ccc(NC(=O)c2ccc(CN3CCOCC3)c(C(F)(F)F)c2)cc1NC(=O)/C=C/c1cncnc1]

The compound was synthesized by reference to example 31.

MS (FAB): 526 (M+1).

Example 42

N-(4-methyl-3-(3-(pyrimidin-5-yl)acrylamido)phenyl)-4-(((R)-3-(dimethylamino)pyrrolidin-1-yl)methyl)-3-(trifluoromethyl)benzamide (Compound 42)

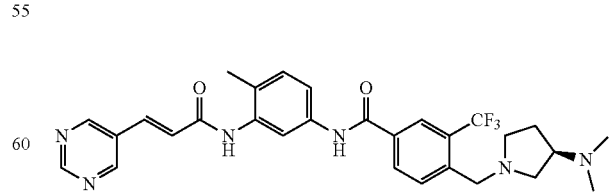

The compound was synthesized by reference to example 31.

MS (FAB): 553 (M+1).

Example 43

N-(4-methyl-3-(3-(pyrimidin-5-yl)acrylamido)phenyl)-4-(((S)-3-(dimethylamino)pyrrolidin-1-yl)methyl)-3-(trifluoromethyl)benzamide (Compound 43)

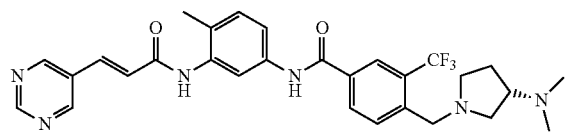

The compound was synthesized by reference to example 31.
MS (FAB): 553 (M+1).

Example 44

N-(4-methyl-3-(3-(pyrimidin-5-yl)acrylamido)phenyl)-4-((3-(dimethylamino)pyrrolidin-1-yl)methyl)-3-(trifluoromethyl)benzamide (Compound 44)

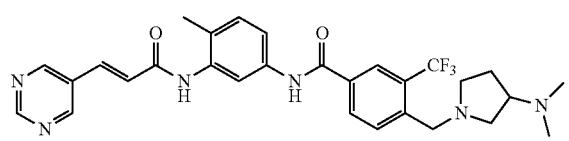 [SMILES: Cc1ccc(NC(=O)c2ccc(CN3CCC(N(C)C)C3)c(C(F)(F)F)c2)cc1NC(=O)/C=C/c1cncnc1]

The compound was synthesized by reference to example 31.
MS (FAB): 553 (M+1).

Example 45

N-(4-methyl-3-(3-(pyrimidin-5-yl)acrylamido)phenyl)-4-((4-methyl-1,4-homopiperazin-1-yl)methyl)-3-(trifluoromethyl)benzamide (Compound 45)

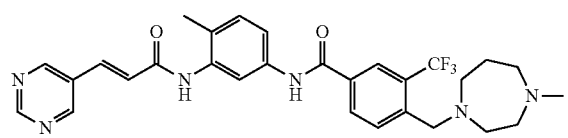 [SMILES: Cc1ccc(NC(=O)c2ccc(CN3CCCN(C)CC3)c(C(F)(F)F)c2)cc1NC(=O)/C=C/c1cncnc1]

The compound was synthesized by reference to example 31.
MS (FAB): 553 (M+1).

Example 46

N-(4-methyl-3-(3-(pyrimidin-5-yl)acrylamido)phenyl)-4-((4-methylpiperazin-1-yl)methyl)-3-bromobenzamide (Compound 46)

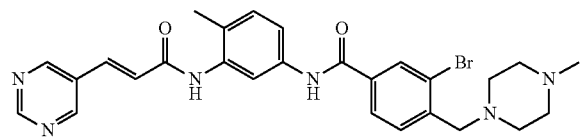 [SMILES: Cc1ccc(NC(=O)c2ccc(CN3CCN(C)CC3)c(Br)c2)cc1NC(=O)/C=C/c1cncnc1]

The compound was synthesized by reference to example 31.
MS (FAB): 550 (M+1).

Example 47

N-(4-methyl-3-(3-(pyrimidin-5-yl)acrylamido)phenyl)-4-((4-methylpiperazin-1-yl)methyl)-3-chlorobenzamide (Compound 47)

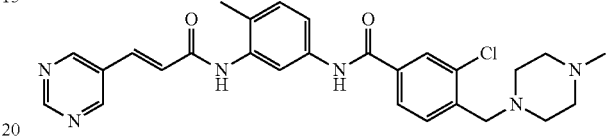

The compound was synthesized by reference to example 31.
MS (FAB): 564 (M+1).

Example 48

N-(4-methyl-3-(3-(pyrimidin-5-yl)acrylamido)phenyl)-4-(morpholin-4-ylmethyl)-3-bromobenzamide (compound 48)

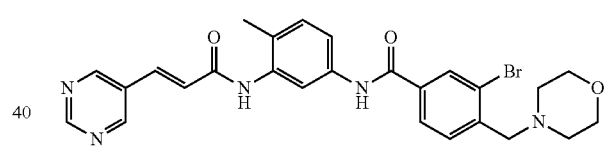

The compound was synthesized by reference to example 31.
MS (FAB): 537 (M+1).

Example 49

N-(4-methyl-3-(3-(pyrimidin-5-yl)acrylamido)phenyl)-4-((4-methyl-1,4-homopiperazin-1-yl)methyl)-3-bromobenzamide (Compound 49)

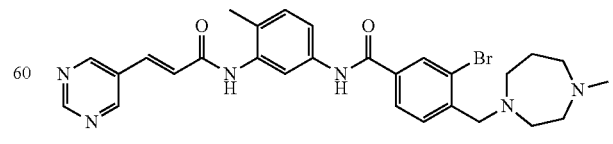

The compound was synthesized by reference to example 31.
MS (FAB): 564 (M+1).

Example 50

Synthesis of N-(3-chloro-4-fluorophenyl)-4-methyl-3-(3-(pyridin-3-yl)acrylamido)benzamide (Compound 50)

Step 1. Synthesis of N-(3-chloro-4-fluorophenyl)-4-methyl-3-nitro benzamide

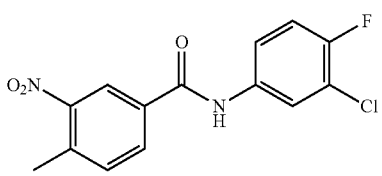 [SMILES: Cc1ccc(C(=O)Nc2ccc(F)c(Cl)c2)cc1[N+](=O)[O-]]

To a solution of 4-methyl-3-nitrobenzoyl chloride (2.0 g) in dichloromethane (20 ml), a solution of triethylamine (0.7 ml) and 3-chloro-4-fluoroaniline (0.7 g) in dichloromethane (15 ml) was added dropwise in an ice-bath with the temperature no more than 5° C. After addition, the reaction was carried out for 30 min in an ice-bath, and then at room temperature overnight. The completion of reaction was indicated by TLC. Then potassium carbonate solution (10%) was added to precipitate a solid. The mixture was left to stand, and filtered. The filter cake was washed with water, and dried to give a pale yellow powdered solid.

Step 2. Synthesis of N-(3-chloro-4-fluorophenyl)-4-methylbenzamide

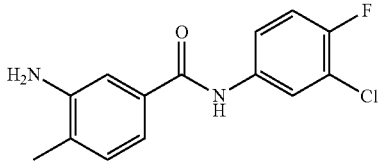

0.7 g of the product of Step 1 was added into 80 ml of ethanol:water (v/v=31), then 1.0 g iron powder and 0.4 g ammonium chloride. After addition, the reaction mixture was heated to 70° C. and reacted for 30 min. The completion of reaction was indicated by TLC. The reaction mixture was filtered, and the filter cake was washed with hot ethanol repeatedly. Then the filtrate was concentrated under reduced pressure to give a white solid. Then 20 ml potassium carbonate solution (10%) was added into the solid. The mixture was stirred, left to stand, filtered, and dried to give a light yellow solid (0.7 g).

Step 3. Synthesis of N-(3-chloro-4-fluorophenyl)-4-methyl-3-(3-(pyridin-3-yl)acrylamido)benzamide

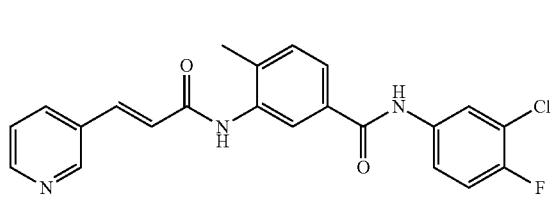 [SMILES: Cc1ccc(C(=O)Nc2ccc(F)c(Cl)c2)cc1NC(=O)/C=C/c1cccnc1]

To a solution of the product of step 2 (0.7 g) and anhydrous triethylamine (0.7 ml) in dichloromethane (20 ml), 3-pyridin-3-ylacryloyl chloride hydrochloride (1.2 g) was added in batches in an ice-bath with the temperature no more than 5° C. After addition, the reaction was carried out for 30 min in an ice-bath, and then at room temperature overnight. The completion of reaction was indicated by TLC. Then potassium carbonate solution (10%) was added. The mixture was extracted with EtOAc (20 ml*3). The organic layer was dried over anhydrous $MgSO_4$, filtered, and concentrated under reduced pressure to recover solvent. The residue was purified on silica gel column using EtOAc/petroleum ether/ethanol (2:1:5) as an eluent. The concentration of the eluent and crystallization provided a yellow solid powder.

$^1$HNMR (DMSO-$d_6$) (ppm): δ2.34 (s, 3H), δ7.11 (d, 1H), δ7.41-7.45 (m, 2H), δ7.51 (dd, 1H), δ7.66 (d, 1H), δ8.07-8.19 (m, 3H), δ8.60 (dd, 1H), δ8.85 (d, 1H), δ9.97 (s, 1H), δ10.42 (s, 1H).

Example 51

N-(3-(trifluoromethyl)phenyl)-4-methyl-3-(3-(pyridin-3-yl)acrylamido)benzamide (Compound 51)

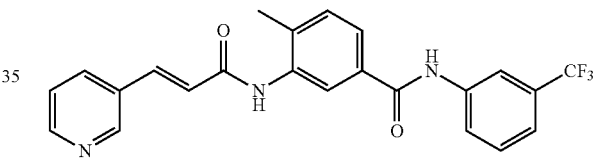

The compound was synthesized by reference to example 50.

$^1$HNMR (DMSO-$d_6$) (ppm): δ2.35 (s, 3H), δ7.11 (d, 1H), δ7.42-7.68 (m, 5H), δ7.76 (dd, 1H), δ8.07 (d, 2H), δ8.22 (d, 1H), δ8.24 (s, 1H), δ8.59 (dd, 1H), δ8.84 (d, 1H), δ9.74 (s, 1H), δ10.50 (s, 1H).

Example 52

N-(4-bromo-2-fluorophenyl)-4-methyl-3-(3-(pyridin-3-yl)acrylamido)benzamide (Compound 52)

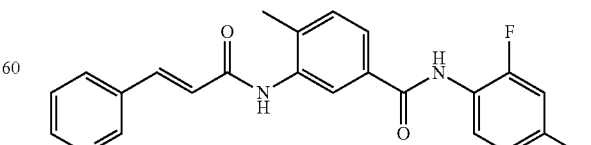

The compound was synthesized by reference to example 50.

¹HNMR (DMSO-d₆) (ppm): δ2.34 (s, 3H), δ7.11 (d, 1H), δ7.40-7.75 (m, 7H), δ8.07 (d, 1H), δ8.21 (s, 1H), δ8.59 (d, 1H), δ8.85 (s, 1H), δ9.78 (s, 1H), δ10.18 (s, 1H).

Example 53

N-(4-(trifluoromethoxy)phenyl)-4-methyl-3-(3-(pyridin-3-yl)acrylamido)benzamide (Compound 53)

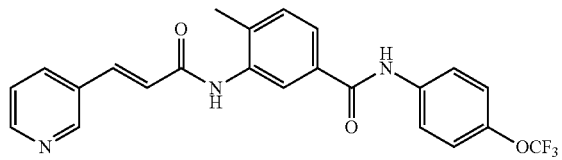 [SMILES: Cc1ccc(C(=O)Nc2ccc(OC(F)(F)F)cc2)cc1NC(=O)/C=C/c1cccnc1]

The compound was synthesized by reference to example 50.

¹HNMR (DMSO-d₆) (ppm): δ2.50 (s, 3H), δ7.12 (d, 1H), δ7.36-7.43 (m, 3H), δ7.50 (dd, 1H), δ7.66 (d, 1H), δ7.74 (dd, 1H), δ7.88-7.91 (m, 2H), δ8.07 (d, 1H), δ8.19 (s, 1H), δ8.59 (dd, 1H), δ8.85 (d, 1H), δ9.79 (s, 1H), δ10.42 (s, 1H).

Example 54

N-(4-(methoxy)phenyl)-4-methyl-3-(3-(pyridin-3-yl)acrylamido)benzamide (Compound 54)

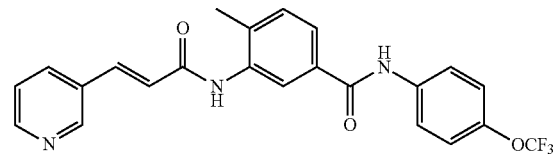 [SMILES: Cc1ccc(C(=O)Nc2ccc(OC(F)(F)F)cc2)cc1NC(=O)/C=C/c1cccnc1]

The compound was synthesized by reference to example 50.

¹HNMR (DMSO-d₆) (ppm): δ2.32 (s, 3H), δ7.09-7.13 (d, 1H), δ7.38-7.51 (d, 1H), δ7.63-7.81 (m, 6H), δ8.05-8.08 (m, 1H), δ8.17 (s, 1H), δ8.59-8.60 (dd, 1H), δ8.85 (s, 1H), δ9.75 (s, 1H), δ10.10-10.12 (d, 1H), δ10.51 (s, 1H).

Example 55

N-(4-(4-methyl-1H-imidazol-1-yl)-3-(trifluoromethyl)phenyl)-4-methyl-3-(3-(pyridin-3-yl)acrylamido)benzamide (Compound 55)

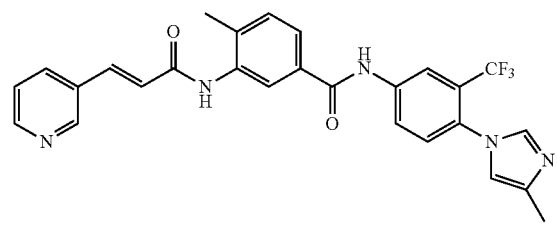 [SMILES: Cc1cn(-c2ccc(NC(=O)c3ccc(C)c(NC(=O)/C=C/c4cccnc4)c3)cc2C(F)(F)F)cn1]

The compound was synthesized by reference to example 50.

¹HNMR (DMSO-d₆) (ppm): δ2.16 (s, 3H), δ2.50 (s, 3H), δ7.15 (d, 1H), δ7.19 (d, 1H), δ7.41-7.83 (m, 5H), δ8.05 (dd, 1H), δ8.20-8.38 (m, 2H), δ8.67 (d, 2H), δ8.93 (d, 2H), δ9.84 (s, 1H), δ10.72 (s, 1H).

Example 56

N-(3,4-dichlorophenyl)-4-methyl-3-(3-(pyridin-3-yl)acrylamido)benzamide (Compound 56)

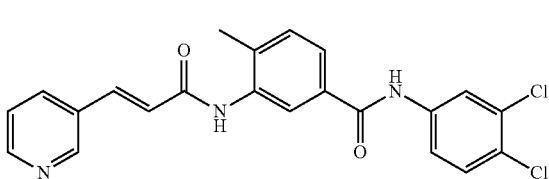

The compound was synthesized by reference to example 50.

¹HNMR (DMSO-d₆) (ppm): δ2.34 (s, 3H), δ7.12 (d, 1H), δ7.41-7.62 (m, 6H), δ8.07 (d, 1H), δ8.18 (d, 2H), δ8.59 (d, 1H), δ8.84 (s, 1H), δ9.69 (s, 1H), δ10.47 (s, 1H).

Example 57

N-(2-chloro-5-(trifluoromethyl)phenyl)-4-methyl-3-(3-(pyridin-3-yl)acrylamido)benzamide (Compound 57)

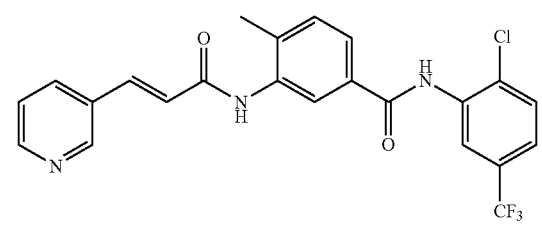 [SMILES: Cc1ccc(C(=O)Nc2cc(C(F)(F)F)ccc2Cl)cc1NC(=O)/C=C/c1cccnc1]

The compound was synthesized by reference to example 50.

¹HNMR (DMSO-d₆) (ppm): δ2.50 (s, 3H), δ6.68 (d, 1H), δ7.011 (d, 1H), δ7.60-7.68 (m, 3H), 7.64 (m, 3H), δ7.77 (dd, 1H), δ8.06 (d, 1H), δ8.58 (d, 1H), δ8.84 (s, 1H), δ9.74 (s, 1H), δ10.22 (s, 1H).

Example 58

N-(4-chloro-3-(trifluoromethyl)phenyl)-4-methyl-3-(3-(pyridin-3-yl)acrylamido)benzamide (Compound 58)

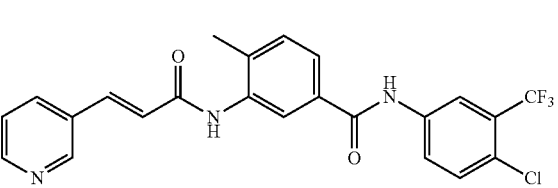

The compound was synthesized by reference to example 50.

¹HNMR (DMSO-d₆) (ppm): δ2.35 (s, 3H), δ7.11 (d, 1H), δ7.44 (d, 1H), δ7.49 (dd, 1H), δ7.64-7.77 (m, 3H), δ8.06-8.08 (m, 1H), δ8.14 (dd, 1H), δ8.22 (s, 1H), δ8.36 (d, 1H), δ8.59 (dd, 1H), δ8.85 (d, 1H), δ9.74 (s, 1H), δ10.59 (s, 1H).

Example 59

N-(3,4-dimethoxyphenyl)-4-methyl-3-(3-(pyridin-3-yl)acrylamido)benzamide (Compound 59)

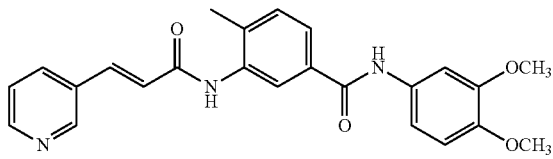 [SMILES: COc1ccc(NC(=O)c2ccc(C)c(NC(=O)/C=C/c3cccnc3)c2)cc1OC]

The compound was synthesized by reference to example 50.

¹HNMR (DMSO-d₆) (ppm): δ2.33 (s, 3H), δ3.75 (s, 6H), δ6.93 (d, 1H), δ7.10 (d, 1H), δ7.35 (dd, 1H), δ7.40 (d, 1H), δ7.45 (d, 1H), δ7.46 (dd, 1H), δ7.65 (d, 1H), δ7.72 (dd, 1H), δ8.07 (d, 1H), δ8.17 (s, 1H), δ8.59 (dd, 1H), δ8.84 (s, 1H), δ9.72 (s, 1H), δ10.05 (s, 1H).

Example 60

N-(4-fluoro-3-(trifluoromethyl)phenyl)-4-methyl-3-(3-(pyridin-3-yl)acrylamido)benzamide (Compound 60)

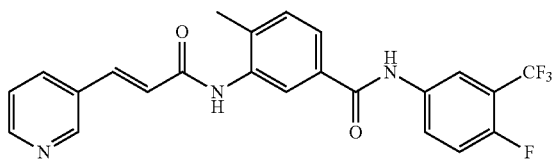 [SMILES: Cc1ccc(C(=O)Nc2ccc(F)c(C(F)(F)F)c2)cc1NC(=O)/C=C/c1cccnc1]

The compound was synthesized by reference to example 50.

¹HNMR (DMSO-d₆) (ppm): δ2.34 (s, 3H), δ7.12 (d, 1H), δ7.44 (d, 1H), δ7.48-7.56 (m, 2H), δ7.66 (d, 1H), δ7.76 (d, 1H), δ8.07 (d, 1H), δ8.12 (t, 1H), δ8.22 (s, 1H), δ8.26 (d, 1H), δ8.60 (d, 1H), δ8.85 (s, 1H), δ9.76 (s, 1H), δ10.54 (s, 1H).

Example 61

N-(3-fluoro-4-methylphenyl)-4-methyl-3-(3-(pyridin-3-yl)acrylamido)benzamide (Compound 61)

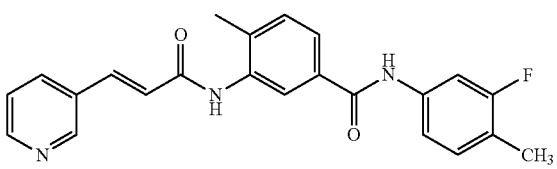 [SMILES: Cc1ccc(NC(=O)c2ccc(C)c(NC(=O)/C=C/c3cccnc3)c2)cc1F]

The compound was synthesized by reference to example 50.

¹HNMR (DMSO-d₆) (ppm): δ2.20 (s, 3H), δ2.34 (s, 3H), δ7.13 (d, 1H), δ7.24 (t, 1H), δ7.39-7.50 (m, 3H), 7.63-7.73 (m, 3H), δ8.07 (d, 1H), δ8.18 (s, 1H), δ8.59 (dd, 1H), δ8.84 (s, 1H), δ10.08 (s, 1H).

Example 62

N-(4-methyl-3-(trifluoromethyl)phenyl)-4-methyl-3-(3-(pyridin-3-yl)acrylamido)benzamide (Compound 62)

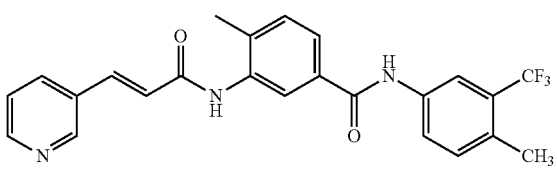 [SMILES: Cc1ccc(C(=O)Nc2ccc(C)c(C(F)(F)F)c2)cc1NC(=O)/C=C/c1cccnc1]

The compound was synthesized by reference to example 50.

¹HNMR (DMSO-d₆) (ppm): δ2.34 (s, 3H), δ2.50 (s, 3H), δ7.13 (d, 1H), δ7.41-7.49 (m, 3H), δ7.65 (d, 1H), δ7.75 (d, 1H), δ7.96-8.21 (m, 4H), δ8.59 (s, 1H), δ8.85 (s, 1H), δ10.17 (s, 2H).

Example 63

N-(3-(4-methyl-1H-imidazol-1-yl)-5-(trifluoromethyl)phenyl)-4-methyl-3-(3-(pyridin-3-yl)acrylamido)benzamide (Compound 63)

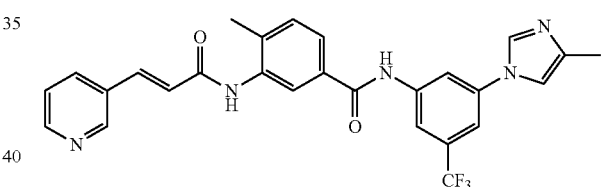

The compound was synthesized by reference to example 50.

¹HNMR (DMSO-d₆) (ppm): δ2.18 (s, 3H), δ2.35 (s, 3H), δ7.12 (d, 1H), δ7.44-7.51 (m, 3H), δ7.64-7.79 (m, 3H), δ8.06-8.30 (m, 5H), δ8.59 (dd, 1H), δ8.85 (d, 1H), δ9.75 (s, 1H), δ10.64 (s, 1H).

Example 64

N-(4-(morpholin-4-ylmethyl)-3-(trifluoromethyl)phenyl)-4-methyl-3-(3-(pyridin-3-yl)acrylamido)benzamide (Compound 64)

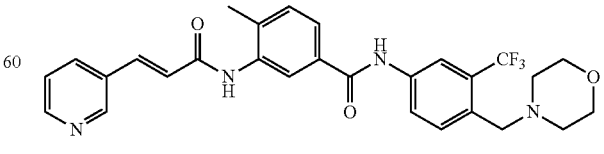

The compound was synthesized by reference to example 50.

MS (FAB): 525 (M+1).

Example 65

N-(4-fluorophenyl)-4-methyl-3-(3-(pyridin-3-yl)acrylamido)benzamide (compound 65)

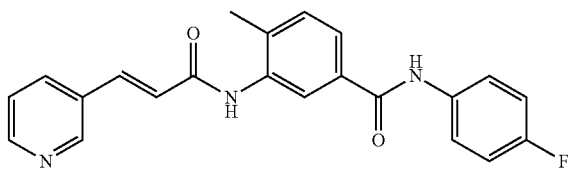 [SMILES: Cc1ccc(C(=O)Nc2ccc(F)cc2)cc1NC(=O)/C=C/c1cccnc1]

Step 1. Synthesis of 4-methyl-3-(3-(pyridin-3-yl)acrylamido)benzoic acid methyl ester

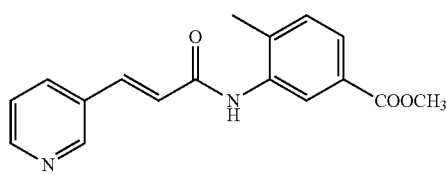 [SMILES: COC(=O)c1ccc(C)c(NC(=O)/C=C/c2cccnc2)c1]

To a suspension of 3-pyridin-3-ylacryloyl chloride hydrochloride (5.1 g) in anhydrous dichloromethane (100 ml), a solution of 3-amino-4-methyl benzoic acid methyl ester (2.75 g) and triethylamine (2.3 ml) in dichloromethane (50 ml) was added dropwise slowly in an ice-bath with the temperature no more than 5° C. After addition, the reaction was carried out for 30 min in an ice-bath, and to then at room temperature for 3 h. The completion of reaction was indicated by TLC. The reaction mixture was concentrated and dissolved into 150 ml of sodium hydroxide solution (10%). The reaction mixture was extracted with EtOAc (30 ml*3). The organic layer was dried over anhydrous MgSO$_4$, and filtered. Most EtOAc was removed by evaporation under reduced pressure. The is residue was cooled in refrigerator. Crystallization and filtration provided a light yellow crystal.

Step 2. Synthesis of 4-methyl-3-(3-(pyridin-3-yl acrylamido)benzoic acid

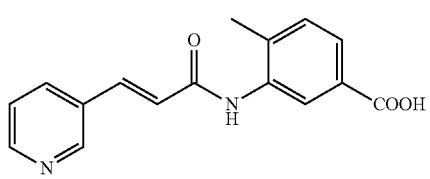 [SMILES: Cc1ccc(C(=O)O)cc1NC(=O)/C=C/c1cccnc1]

3.0 g of the product of step 1 was dissolved into a solution of methanol, tetrahydrofuran, and water (60 ml, 1:1:1) with stirring, then 0.75 g lithium hydroxide was added. The mixture was stirred at room temperature for 4 h. The completion of reaction was indicated by TLC. The reaction solution was acidified with dilute hydrochloric acid to adjust PH to 3-4, so as to precipitate a solid. The mixture was cooled, left to stand, filtered, and dried to give a white solid.

Step 3. Synthesis of 4-methyl-3-(3-(pyridin-3-yl)acrylamido)benzoyl chlorid

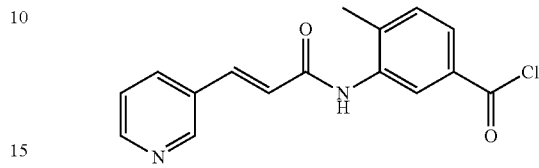

To a suspension of the product of step 2 (2.8 g) and triethylamine (0.5 ml) in anhydrous dichloromethane (30 ml), 5.0 ml of oxalyl chloride was added dropwise slowly in an ice-bath with the temperature no more than 5° C. After addition, the reaction was carried out for 30 min in an ice-bath, and then at room temperature overnight. The completion of reaction was indicated by TLC. The reaction mixture was concentrated under reduced pressure to give a white solid, which was left to stand at room temperature for 1 h and directly used in the next step.

Step 4. Synthesis of N-(4-fluorophenyl)-4-methyl-3-(3-(pyridin-3-yl)acrylamido)benzamide To a suspension of the product of step 3 (0.3 g) in anhydrous dichloromethane (30 ml), a solution of 4-fluoroaniline (0.1 g) and triethylamine (0.2 ml) in dichloromethane (15 ml) was added dropwise slowly in an ice-bath with the temperature no more than 5° C. After addition, the reaction was carried out for 30 min in an ice-bath, and then at room temperature overnight. The completion of reaction was indicated by TLC. Potassium carbonate solution (10%) was added. The reaction mixture was extracted with EtOAc (20 ml*3). The organic layer was dried over anhydrous MgSO$_4$, filtered, and concentrated under reduced pressure to recover solvent. The residue was purified on a silica gel column using EtOAc/petroleum ether/ethanol (1:2:0.5) as an eluent. The concentration of the eluent and crystallization provided a solid powder.

$^1$HNMR (DMSO-d$_6$) (ppm): δ2.34 (s, 3H), δ7.11 (d, 1H), δ7.18-7.22 (m, 2H), δ7.41 (d, 1H), δ7.50 (dd, 1H), δ7.66 (d, 1H), δ7.72-7.81 (m, 3H), δ8.07 (d, 2H), δ7.19 (s, 1H), δ8.60 (dd, 1H), δ8.85 (d, 1H), δ9.76 (s, 1H), δ10.28 (s, 1H).

Example 66

N-(4-(methyl)phenyl)-4-methyl-3-(3-(pyridin-3-yl)acrylamido)benzamide (compound 66)

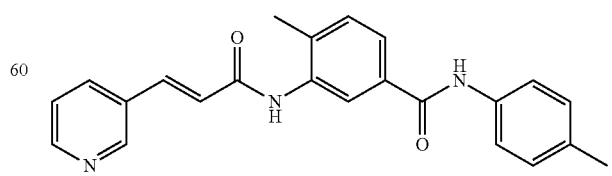

The compound was synthesized by reference to example 65.

¹HNMR (DMSO-d) (ppm): δ2.50 (s, 6H), δ7.09-7.16 (m, 3H), δ7.400 (d, 1H), δ7.50 (dd, 1H), δ7.64-7.67 (m, 3H), δ7.72 (dd, 1H), δ8.07 (d, 1H), δ8.17 (s, 1H), δ8.59 (dd, 1H), δ8.84 (d, 1H), δ9.75 (s, 1H), δ10.14 (s, 1H).

Example 67

N-(2-chloro-6-methylphenyl)-4-methyl-3-(3-(pyridin-3-yl)acrylamido)benzamide (Compound 67)

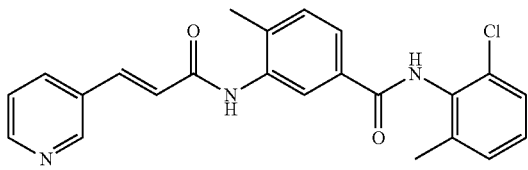 [SMILES: Cc1ccc(C(=O)Nc2c(C)cccc2Cl)cc1NC(=O)/C=C/c1cccnc1]

The compound was synthesized by reference to example 65.

¹HNMR (DMSO-d₆) (ppm): δ2.11 (s, 3H), δ2.32 (s, 3H), δ5.76 (s, 1H), δ7.11 (d, 1H), δ7.17-7.26 (m, 2H), δ7.37 (t, 2H), δ7.64 (d, 1H), δ7.78 (d, 1H), δ8.06 (d, 1H), δ8.17 (s, 1H), δ8.58 (dd, 1H), δ8.83 (d, 1H), δ9.83 (s, 1H).

Example 68

N-(3-fluorophenyl)-4-methyl-3-(3-(pyridin-3-yl)acrylamido)benzamide (Compound 68)

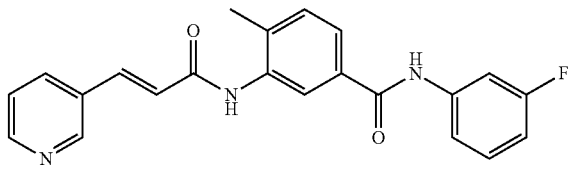 [SMILES: Cc1ccc(C(=O)Nc2cccc(F)c2)cc1NC(=O)/C=C/c1cccnc1]

The compound was synthesized by reference to example 65.

¹HNMR (DMSO-d₆) (ppm): δ2.50 (s, 3H), δ7.09-7.13 (m, 5H), δ7.66 (d, 2H), δ7.68-7.78 (m, 2H), δ8.07 (d, 1H), δ7.20 (s, 1H), δ8.59 (dd, 1H), δ8.85 (d, 1H), δ9.77 (s, 1H), δ10.41 (s, 1H).

Example 69

N-(4-(morpholin-4-yl)-3-(trifluoromethyl)phenyl)-4-methyl-3-(3-(pyridin-3-yl)acrylamido)benzamide (Compound 69)

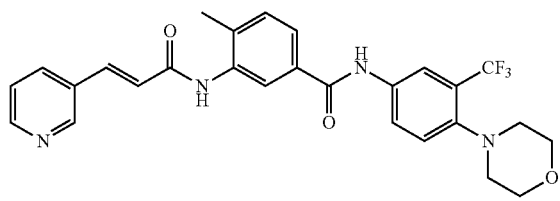 [SMILES: Cc1ccc(C(=O)Nc2ccc(N3CCOCC3)c(C(F)(F)F)c2)cc1NC(=O)/C=C/c1cccnc1]

The compound was synthesized by reference to example 65.

¹HNMR (DMSO-d₆) (ppm): δ2.34 (s, 3H), δ2.84 (t, 4H), δ3.70 (t, 4H), δ7.12 (d, 1H), δ7.42-7.70 (m, 5H), δ8.06-8.21 (m, 4H), δ8.60 (dd, 1H), δ8.85 (d, 1H), δ9.78 (s, 1H), δ10.45 (s, 1H).

Example 70

N-((3-(piperidin-1-yl)methyl)phenyl)-4-methyl-3-(3-(pyridin-3-yl)acrylamido)benzamide (Compound 70)

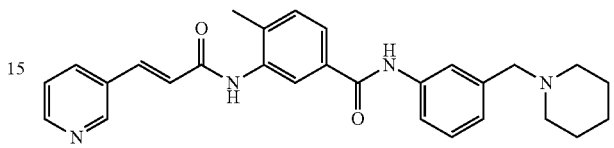

The compound was synthesized by reference to example 65.

¹HNMR (DMSO-d₆) (ppm): δ1.39-1.51 (m, 6H), δ2.33-2.50 (m, 7H), δ3.37 (s, 2H), δ7.00 (d, 1H), δ57.12 (d, 1H), δ7.27 (t, 1H), δ7.40 (d, 1H), δ7.49 (dd, 1H), δ7.64-7.76 (m, 4H), δ8.07 (d, 1H), δ8.20 (s, 1H), δ8.59 (dd, 1H), δ8.85 (d, 1H), δ9.77 (s, 1H), δ10.19 (s, 1H).

Example 71

N-(4-(4-methylpiperazin-1-yl)-3-(trifluoromethyl)phenyl)-4-methyl-3-(3-(pyridin-3-yl)acrylamido)benzamide (Compound 71)

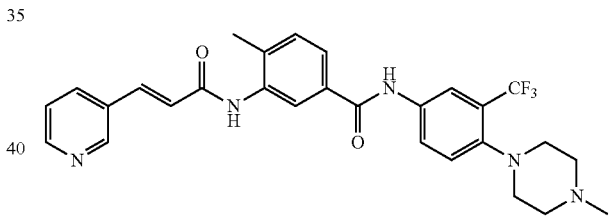

The compound was synthesized by reference to example 65.

¹HNMR (DMSO-d₆) (ppm): δ2.21 (s, 3H), δ2.34 (s, 3H), δ2.84 (t, 4H), δ7.12 (d, 1H), δ7.41-7.76 (m, 5H), δ8.04-8.20 (m, 4H), δ8.59 (dd, 1H), δ8.85 (d, 1H), δ9.79 (s, 1H), δ10.43 (s, 1H).

Example 72

N-(3-((4-methylpiperazin-1-yl)methyl)phenyl)-4-methyl-3-(3-(pyridin-3-yl)acrylamido)benzamide (Compound 72)

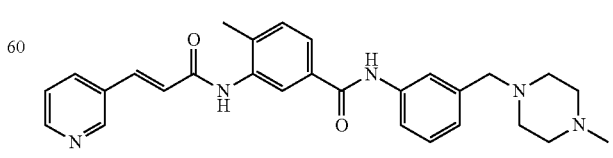

The compound was synthesized by reference to example 65.

¹HNMR (DMSO-d₆) (ppm): δ2.07 (s, 3H), δ2.33 (t, 4H), δ2.43-2.50 (m, 7H), δ3.36 (s, 2H), δ7.01 (d, 1H), δ7.11 (d, 1H), δ7.28 (t, 1H), δ740 (d, 1H), δ7.49 (dd, 1H), δ7.64-7.76 (m, 4H), δ8.07 (d, 1H), δ8.19 (s, 1H), δ8.59 (dd, 1H), δ8.85 (d, 1H), δ9.77 (s, 1H), δ10.20 (s, 1H).

Example 73

N-(4-(morpholin-4-ylmethyl)phenyl)-4-methyl-3-(3-(pyridin-3-yl)acrylamido)benzamide (Compound 73)

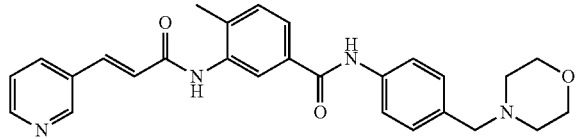 [SMILES: Cc1ccc(C(=O)Nc2ccc(CN3CCOCC3)cc2)cc1NC(=O)/C=C/c1cccnc1]

The compound was synthesized by reference to example 65.

¹HNMR (CDCl₃) (ppm): δ2.33 (s, 3H), δ2.47 (t, 4H), δ3.50 (s, 2H), δ3.72 (t, 4H), δ6.76 (d, 1H), δ7.26-7.32 (m, 5H), δ7.61-7.89 (m, 6H), δ8.23 (s, 1H), δ8.57 (dd, 1H), δ8.74 (s, 1H).

Example 74

N-(4-(4-ethylpiperazin-1-yl)-3-(trifluoromethyl)phenyl)-4-methyl-3-(3-(pyridin-3-yl)acrylamido)benzamide (Compound 74)

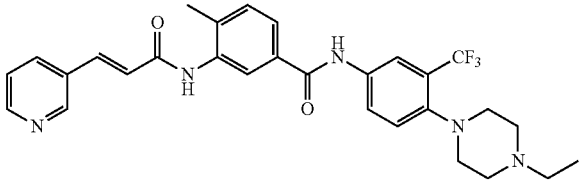 [SMILES: CCN1CCN(c2ccc(NC(=O)c3ccc(C)c(NC(=O)/C=C/c4cccnc4)c3)cc2C(F)(F)F)CC1]

The compound was synthesized by reference to example 65.

¹HNMR (DMSO-d₆) (ppm): δ0.84 (t, 3H), δ1.05 (q, 2H), δ2.50 (s, 3H), δ2.51 (t, 4H), δ2.87 (t, 4H), δ7.12 (d, 1H), δ7.42 (d, 1H), δ7.50 (dd, 1H), δ7.58 (d, 1H), δ7.66 (d, 1H), 7.75 (dd, 1H), δ8.06-8.20 (m, 4H), δ8.60 (dd, 1H), δ8.84 (d, 1H), δ9.78 (s, 1H), δ10.44 (s, 1H).

Example 75

N-(2,6-dimethylphenyl)-4-methyl-3-(3-(pyridin-3-yl)acrylamido)benzamide (Compound 75

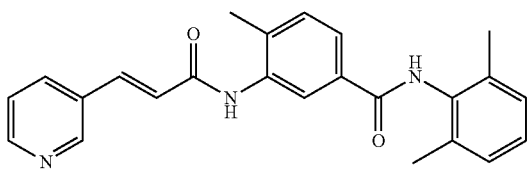 [SMILES: Cc1ccc(C(=O)Nc2c(C)cccc2C)cc1NC(=O)/C=C/c1cccnc1]

The compound was synthesized by reference to example 65.

¹HNMR ((DMSO-d₆) (ppm): δ2.18 (s, 6H), δ2.33 (s, 3H), δ7.08-7.12 (m, 4H), δ7.40 (d, 1H), δ7.49 (dd, 1H), δ7.65 (d, 1H), δ7.78 (dd, 1H), δ8.07 (d, 1H), δ8.20 (s, 1H), δ8.59 (dd, 1H), δ8.84 (d, 1H), δ9.76 (d, 2H).

Example 76

N-(3,5-di-(trifluoromethyl)phenyl)-4-methyl-3-(3-(pyridin-3-yl)acrylamido)benzamide (Compound 76)

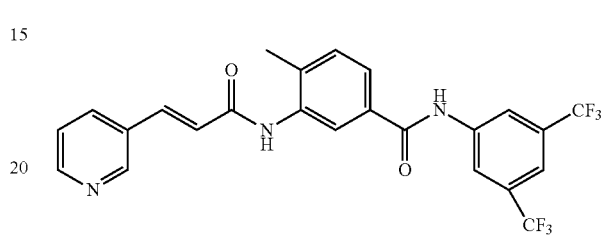

The compound was synthesized by reference to example 65.

¹HNMR (DMSO-d₆) (ppm): δ2.35 (s, 3H), δ7.15 (d, 1H), δ2.87 (t, 4H), δ7.46 (d, 2H), δ7.66 (d, 1H), δ7.79 (t, 2H), δ8.07 (d, 1H), δ8.26 (s, 1H), δ8.56 (d, 3H), δ8.84 (s, 1H), δ9.82 (sd, 1H), δ10.84 (s, 1H).

Example 77

Synthesis of N-(4-methyl-3-(trifluoromethyl)phenyl)-4-methyl-3-(3-(pyrimidin-5-yl)acrylamido)benzamide (Compound 77)

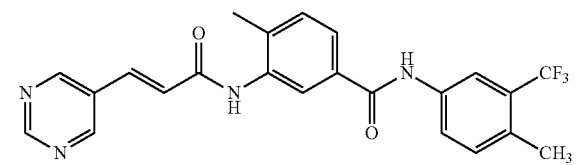 [SMILES: Cc1ccc(C(=O)Nc2ccc(C)c(C(F)(F)F)c2)cc1NC(=O)/C=C/c1cncnc1]

N-(4-methyl-3-(trifluoromethyl)phenyl)-3-amino-4-methylbenzamide was synthesized by reference to example 50. To a solution of N-(4-methyl-3-(trifluoromethyl)phenyl)-3-amino-4-methylbenzamide (0.4 g) and triethylamine (0.8 ml) in dichloromethane (20 ml), 3-pyrimidin-5-ylacryloyl chloride hydrochloride (0.5 g) was added in batches in an ice-bath with the temperature no more than 5° C. After addition, the reaction was carried out for 30 min in an ice-bath, and then at room temperature overnight. The completion of reaction was indicated by TLC. Then potassium carbonate solution (10%) was added. The reaction mixture was extracted with EtOAc (20 ml*3). The organic layer was dried over anhydrous Na₂SO₄, filtered, and concentrated under reduced pressure to recover the solvent. The residue was purified on silica gel column using EtOAc/petroleum ether (2:1) as eluent. The concentration of the eluent and crystallization provided a yellow solid powder.

¹HNMR (DMSO-d₆) (ppm): δ2.34 (s, 3H), δ2.50 (s, 3H), δ7.21 (d, 1H), δ7.41-7.43 (m, 2H), δ7.664 (d, 1H), δ7.76 (dd, 1H), δ7.97 (dd, 1H), δ8.18 (t, 2H), δ9.10 (s, 2H), δ9.19 (s, 1H), δ9.83 (s, 1H), δ10.41 (s, 1H).

Example 78

N-(4-(morpholin-4-yl)-3-(trifluoromethyl)phenyl)-4-methyl-3-(3-(pyrimidin-5-yl)acrylamido)benzamide (compound 78)

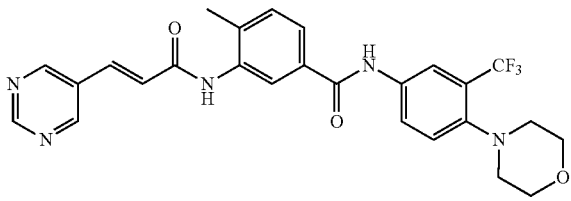 [SMILES: Cc1ccc(C(=O)Nc2ccc(N3CCOCC3)c(C(F)(F)F)c2)cc1NC(=O)/C=C/c1cncnc1]

The compound was synthesized by reference to example 77.

$^1$HNMR (DMSO-d$_6$) (ppm): δ2.34 (s, 3H), δ2.51 (t, 4H), δ3.70 (t, 4H), δ7.19 (d, 1H), δ7.43 (d, 1H), δ7.59-7.77 (m, 4H), δ8.07 (dd, 1H), δ8.17 (d, 1H), δ8.19 (d, 1H), δ9.09 (s, 2H), δ9.19 (s, 1H), δ9.82 (s, 1H), δ10.42 (s, 1H).

Example 79

N-(4-chloro-3-(trifluoromethyl)phenyl)-4-methyl-3-(3-(pyrimidin-5-yl)acrylamido)benzamide (Compound 79)

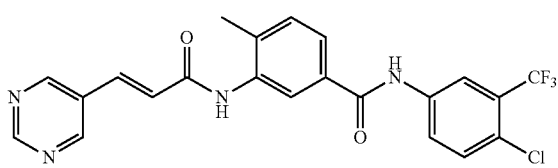

The compound was synthesized by reference to example 77.

$^1$HNMR (DMSO-d$_6$) (ppm): δ2.49 (s, 3H), δ7.20 (d, 1H), δ7.45 (d, 1H), δ7.65 (d, 1H), δ7.71-7.79 (m, 2H), δ8.14 (dd, 1H), δ8.20 (s, 1H), δ8.37 (d, 1H), δ9.11 (s, 2H), δ9.20 (s, 1H), δ9.86 (s, 1H), δ10.62 (s, 1H).

Example 80

N-(3-fluoro-4-methylphenyl)-4-methyl-3-(3-(pyrimidin-5-yl)acrylamido)benzamide (Compound 80)

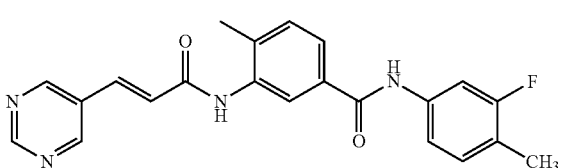

The compound was synthesized by reference to example 77.

$^1$HNMR (DMSO-d$_6$) (ppm): δ2.20 (s, 3H), δ2.33 (s, 3H), δ7.19 (d, 1H), δ7.25 (d, 1H), δ7.42 (d, 1H), δ7.47 (dd, 1H), δ7.64 (d, 1H), δ7.68-7.75 (m, 2H), δ8.16 (d, 1H), δ9.10 (s, 2H), δ9.19 (s, 1H), δ9.84 (s, 1H), δ10.32 (s, 1H).

Example 81

N-(3-chloro-4-fluorophenyl)-4-methyl-3-(3-(pyrimidin-5-yl)acrylamido)benzamide (Compound 81)

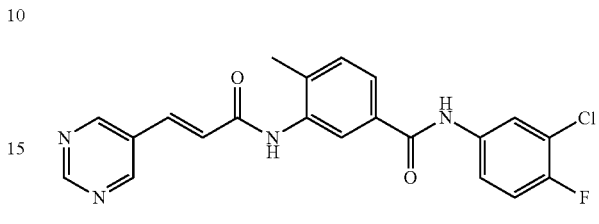

The compound was synthesized by reference to example 77.

$^1$HNMR (DMSO-d$_6$) (ppm): δ2.34 (s, 3H), δ7.20 (d, 1H), δ7.23-7.43 (m, 4H), δ7.64 (d, 1H), δ7.72-7.76 (m, 2H), δ8.08 (dd, 1H), δ8.17 (s, 1H), δ9.10 (s, 2H), δ9.19 (s, 1H), δ9.82 (s, 1H), δ10.39 (s, 1H).

Example 82

N-(2-chloro-6-methylphenyl)-4-methyl-3-(3-(pyrimidin-5-yl)acrylamido)benzamide (Compound 82)

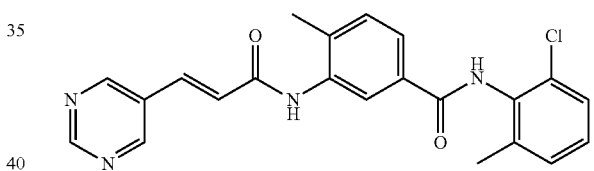

The compound was synthesized by reference to example 77.

$^1$HNMR (DMSO-d$_6$) (ppm): δ2.23 (s, 3H), δ2.33 (s, 3H), δ7.19 (d, 1H), δ7.23-7.43 (m, 4H), δ7.64 (d, 1H), δ7.80 (dd, 1H), δ8.18 (s, 1H), δ9.09 (s, 2H), δ9.19 (s, 1H), δ9.84 (s, 1H), δ9.99 (s, 1H).

Example 83

N-(3,4-dichlorophenyl)-4-methyl-3-(3-(pyrimidin-5-yl)acrylamido)benzamide (Compound 83)

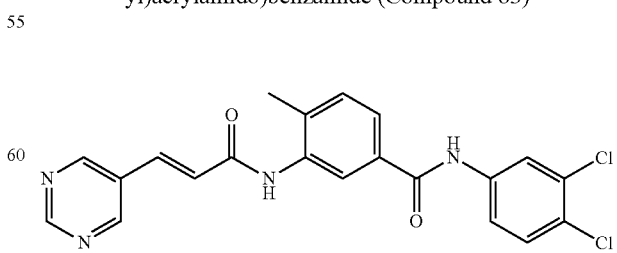

The compound was synthesized by reference to example 77.

¹HNMR (DMSO-d₆) (ppm): δ2.34 (s, 3H), δ7.20 (d, 1H), δ7.43 (d, 1H), δ7.70 (m, 5H), δ8.17 (dd, 2H), δ8.18 (s, 1H), δ9.10 (s, 1H), δ9.19 (s, 1H), δ9.29 (s, 1H), δ9.82 (s, 1H), δ10.46 (s, 1H).

Example 84

N-(4-trifluoromethoxyphenyl)-4-methyl-3-(3-(pyrimidin-5-yl)acrylamido)benzamide (Compound 84)

The compound was synthesized by reference to example 77.

¹HNMR (DMSO-d₆) (ppm): δ2.34 (s, 3H), δ7.20 (d, 1H), δ7.37 (d, 2H), δ7.43 (d, 1H), δ7.65 (d, 1H), δ7.75 (dd, 1H), δ7.90 (d, 2H), δ88.18 (s, 1H), δ9.10 (s, 2H), δ9.19 (s, 1H), δ9.84 (s, 1H), δ10.41 (s, 1H).

Example 85

N-(4-methylphenyl)-4-methyl-3-(3-(pyrimidin-5-yl)acrylamido)benzamide (Compound 85)

The compound was synthesized by reference to example 77.

¹HNMR (DMSO-d₆) (ppm): δ2.30 (s, 6H), δ7.16 (d, 2H), δ7.19 (d, 1H), δ7.40 (d, 1H), δ7.64 (m, 3H), δ7.74 (dd, 1H), δ8.15 (s, 1H), δ9.10 (s, 2H), δ9.19 (s, 1H), δ9.83 (s, 1H), δ10.14 (s, 1H).

Example 86

N-(4-fluorophenyl)-4-methyl-3-(3-(pyrimidin-5-yl)acrylamido)benzamide (Compound 86)

The compound was synthesized by reference to example 77.

MS (FAB): 377 (M+1).

Example 87

N-(4-bromo-2-fluorophenyl)-4-methyl-3-(3-(pyrimidin-5-yl)acrylamido)benzamide (Compound 87)

The compound was synthesized by reference to example 77.

¹HNMR (DMSO-d₆) (ppm): δ2.33 (s, 3H), δ7.19 (d, 1H), δ7.43 (m, 2H), δ7.61 (m, 3H), δ7.75 (dd, 1H), δ8.18 (d, 1H), δ9.09 (s, 2H), δ9.18 (s, 1H), δ9.81 (s, 1H), δ10.14 (s, 1H).

Example 88

N-(3-(trifluoromethyl)phenyl)-4-methyl-3-(3-(pyrimidin-5-yl)acrylamido)benzamide (Compound 88)

The compound was synthesized by reference to example 77.

¹HNMR (DMSO-d₆) (ppm): δ2.50 (s, 3H), δ7.20 (d, 1H), δ7.55 (m, 4H), δ7.73 (dd, 1H), δ8.07 (d, 1H), δ8.23 (d, 2H), δ9.10 (s, 1H), δ9.19 (s, 1H), δ9.30 (s, 1H), δ9.85 (s, 1H), δ10.53 (s, 1H).

Example 89

N-(3-3-fluorophenyl)-4-methyl-3-(3-(pyrimidin-5-yl)acrylamido)benzamide (Compound 89)

The compound was synthesized by reference to example 77.

$^1$HNMR (DMSO-d$_6$) (ppm): δ2.50 (s, 3H), δ6.95 (m, 1H), δ7.21 (d, 2H), δ7.40 (m, 2H), δ7.57 (dd, 1H), δ7.65 (d, 1H), δ7.75 (m, 2H), δ8.17 (s, 1H), δ9.10 (s, 2H), δ9.19 (s, 1H), δ9.86 (s, 1H), δ10.42 (s, 1H).

Example 90

N-(3-(4-methyl-1H-imidazol-1-yl)-5-(trifluoromethyl)phenyl)-4-methyl-3-(3-(pyrimidin-5-yl)acrylamido)benzamide (Compound 90)

The compound was synthesized by reference to example 77.

MS (FAB): 507 (M+1).

Example 91

N-(3,5-di-(trifluoromethyl)phenyl)-4-methyl-3-(3-(pyrimidin-5-yl)acrylamido)benzamide (Compound 91)

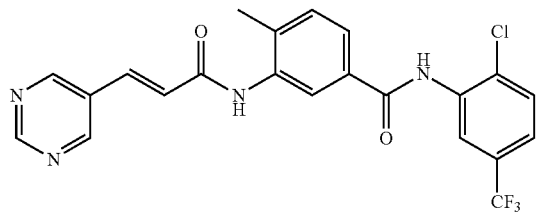 [SMILES: Cc1ccc(C(=O)Nc2cc(C(F)(F)F)ccc2Cl)cc1NC(=O)/C=C/c1cncnc1]

The compound was synthesized by reference to example 77.

MS (FAB): 494 (M+1).

Example 92

N-(4-fluoro-3-(trifluoromethyl)phenyl)-4-methyl-3-(3-(pyrimidin-5-yl)acrylamido)benzamide (Compound 92)

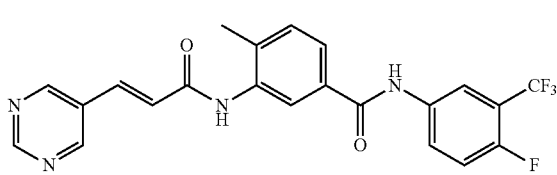 [SMILES: Cc1ccc(C(=O)Nc2ccc(F)c(C(F)(F)F)c2)cc1NC(=O)/C=C/c1cncnc1]

The compound was synthesized by reference to example 77.

MS (FAB): 445 (M+1).

Example 93

N-(4-(4-methylpiperazin-1-yl)-3-(trifluoromethyl)phenyl)-4-methyl-3-(3-(pyrimidin-5-yl)acrylamido)benzamide (Compound 93)

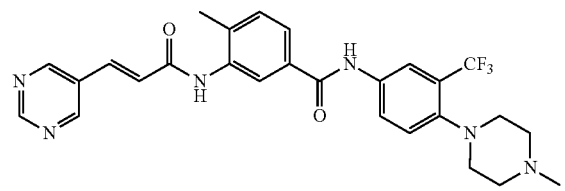 [SMILES: Cc1ccc(C(=O)Nc2ccc(N3CCN(C)CC3)c(C(F)(F)F)c2)cc1NC(=O)/C=C/c1cncnc1]

The compound was synthesized by reference to example 77.

MS (FAB): 525 (M+1).

Example 94

N-(4-(4-methyl-1H-imidazol-1-yl)-3-(trifluoromethyl)phenyl)-4-methyl-3-(3-(pyrimidin-5-yl)acrylamido)benzamide (Compound 94)

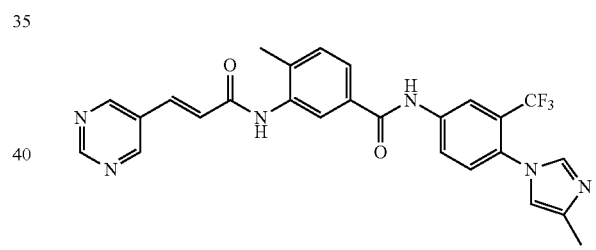

The compound was synthesized by reference to example 77.

MS (FAB): 507 (M+1).

Example 95

N-((3-chloro-4-methyl)phenyl)-4-methyl-3-(3-(pyrimidin-5-yl)acrylamido)benzamide (Compound 95)

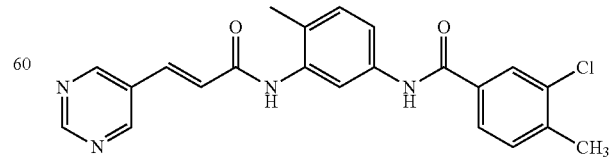

The compound was synthesized by reference to example 77.

¹HNMR (DMSO-d₆) (ppm): δ2.23 (s, 3H), δ2.49 (s, 3H), δ6.95 (m, 1H), δ7.21 (t, 2H), δ7.51-7.63 (m, 3H), δ7.85 (dd, 1H), δ8.03 (t, 2H), δ9.09 (s, 2H), δ9.19 (s, 1H), δ9.68 (s, 1H), δ10.30 (s, 1H).

Example 96

N-((3-bromo-4-methyl)phenyl)-4-methyl-3-(3-(pyrimidin-5-yl)acrylamido)benzamide (Compound 96)

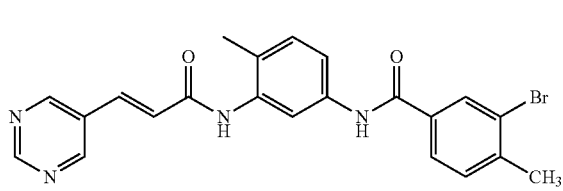 [SMILES: Cc1ccc(C(=O)Nc2ccc(C)c(NC(=O)/C=C/c3cncnc3)c2)cc1Br]

The compound was synthesized by reference to example 77.
¹HNMR (DMSO-d) (ppm): δ2.22 (s, 3H), δ2.50 (s, 3H), δ7.21 (t, 2H), δ7.51-7.63 (m, 3H), δ7.89 (dd, 1H), δ8.02 (d, 1H), δ8.19 (d, 1H), δ9.09 (s, 2H), δ9.19 s, 1H), δ10.30 (s, 1H).

Example 97

N-((3-bromo-4-methyl)phenyl)-4-methyl-3-(3-(pyridin-3-yl)acrylamido)benzamide (Compound 97)

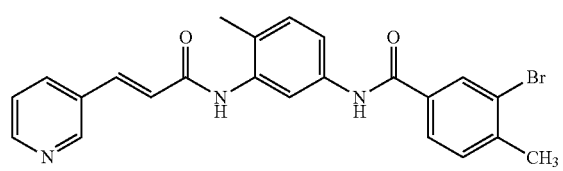 [SMILES: Cc1ccc(C(=O)Nc2ccc(C)c(NC(=O)/C=C/c3cccnc3)c2)cc1Br]

The compound was synthesized by reference to example 1.
¹HNMR (DMSO-d₆) (ppm): δ2.23 (s, 3H), δ2.50 (s, 3H), δ7.10 (d, 1H), δ7.21 (d, 1H), δ7.49-7.65 (m, 4H), δ7.89 (dd, 1H), δ7.53-7.57 (m, 2H), δ7.63 (dd, 1H), δ7.90 (dd, 1H), δ8.05-8.07 (m, 2H), δ8.19 (d, 1H), δ8.59 (dd, 1H), δ8.83 (d, 1H), δ9.60 (s, 1H), δ10.30 (s, 1H).

Example 98

Synthesis of N-(5-(3-(3-trifluoromethyl)phenyl)ureido)-2-methyl phenyl)-3-(pyridin-3-yl)acrylamide (Compound 98)

Step 1. Synthesis of 1-isocyanato-3-trifluoromethyl benzene

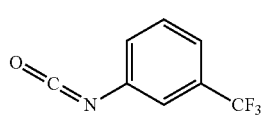 [SMILES: O=C=Nc1cccc(C(F)(F)F)c1]

Triphosgene (0.75 g) was added to anhydroue toluene (10 ml) under nitrogen protection, and then a solution of 3-trifluoromethylaniline (0.8 g) in dichloromethane (15 ml) was added dropwise in an ice-bath. After addition, the reaction mixture was stirred at room temperature for 15 min, and then heated to 80° C. for 6 h. The completion of the reaction was indicated by TLC. The reaction mixture was concentrated under reduced pressure to give the product as oil, which then was solidified.

Step 2. Synthesis of N-(2-methyl-5-(3-(3-trifluoromethyl)phenyl)ureido)phenyl)-3-(pyridin-3-yl)acrylamide

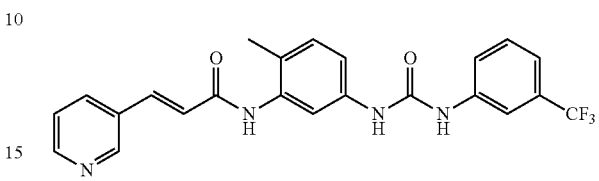

N-(5-amino-2-methylphenyl)-3-pyridinylacrylamide (0.5 g) and the product of step 1 (0.17 g) was added into 20 ml of anhydrouse DMF, and then 0.3 ml triethylamine was added dropwise. After addition, the reaction was carried out at room temperature overnight. The completion of the reaction was indicated by TLC. Then 25 ml water was added to precipitate a solid. The mixture was left to stand and filtered to collect the solid, which was purified on silica gel column using EtOAc/petroleum ether/Ethanol (1:2:0.5) as an eluent. The concentration of the eluent provided a solid.
¹HNMR (DMSO-d₆) (ppm): δ2.20 (s, 3H), δ7.09-7.31 (m, 4H), δ7.47-7.64 (m, 4H), δ7.79 (s, 1H), δ8.05 (d, 2H), δ8.59 (dd, 1H), δ8.83 (s, 2H), δ8.99 (s, 1H), δ9.53 (s, 1H).

Example 99

N-(5-(3-(2-chloro-5-(trifluoromethyl)phenyl)ureido)-2-methyl phenyl)-3-(pyridin-3-yl)acrylamide (Compound 99)

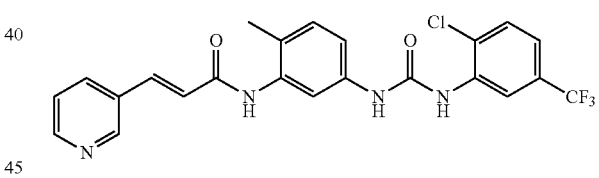

The compound was synthesized by reference to example 98.
¹HNMR (DMSO-d₆) (ppm): δ2.22 (s, 3H), δ7.10-7.17 (q, 2H), δ7.27 (dd, 1H), δ7.36 (dd, 1H), δ7.48 (dd, 1H), δ7.63 (d, 1H), δ7.71 (d, 1H), δ7.84 (s, 1H), δ8.05 (d, 1H), δ8.55-8.66 (m, 3H), δ8.83 (d, 1H), δ9.48 (s, 1H), δ9.59

Example 100

N-(5-(3-(4-(trifluoromethoxy)phenyl)ureido)-2-methylphenyl)-3-(pyridin-3-yl)acrylamide (Compound 100)

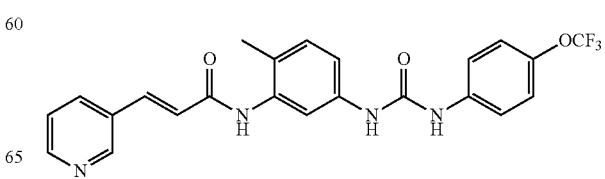

The compound was synthesized by reference to example 98.

¹HNMR (DMSO-d₆) (ppm): δ2.19 (s, 3H), δ7.08-7.28 (m, 5H), δ7.47-7.75 (m, 5H), δ8.05 (d, 1H), δ8.58 (dd, 1H), δ8.72 (s, 1H), δ8.82 (d, 2H), δ9.49 (s, 1H).

Example 101

N-(2-methyl-5-(3-(5-methylisoxazol-3-yl)ureido)phenyl)-3-(pyridin-3-yl)acrylamide (compound 101)

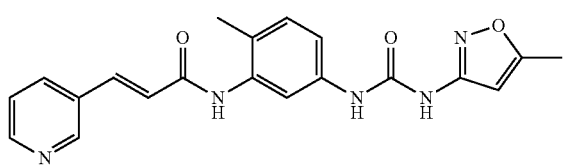 [SMILES: Cc1cc(NC(=O)Nc2ccc(C)c(NC(=O)/C=C/c3cccnc3)c2)no1]

The compound was synthesized by reference to example 98.

¹HNMR (DMSO-d₆) (ppm): δ2.20 (s, 3H), δ2.36 (s, 3H), δ6.54 (s, 1H), δ7.08-7.24 (m, 3H), δ7.49 (dd, 1H), δ7.62 (d, 1H), δ7.75 (s, 1H), δ8.05 (d, 1H), δ8.58 (d, 1H), δ8.83 (d, 2H), δ9.38 (s, 1H), δ9.53 (s, 1H).

Example 102

N-(5-(3-(3-chloro-4-fluorophenyl)ureido)-2-methylphenyl)-3-(pyridin-3-yl)acrylamide (Compound 102)

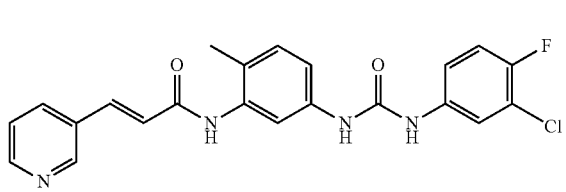 [SMILES: Cc1ccc(NC(=O)Nc2ccc(F)c(Cl)c2)cc1NC(=O)/C=C/c1cccnc1]

The compound was synthesized by reference to example 98.

¹HNMR (DMSO-d₆) (ppm): δ2.19 (s, 3H), δ7.12 (t, 2H), δ7.22-7.33 (m, 3H), δ7.49 (dd, 1H), δ7.62 (d, 1H), δ7.76 (d, 1H), δ7.81 (dd, 1H), δ8.05 (d, 1H), δ8.59 (dd, 1H), δ8.79-8.83 (m, 3H), δ9.52 (s, 1H).

Example 103

N-(5-(3-(5-bromo-2-fluorophenyl)ureido)-2-methylphenyl)-3-(pyridin-3-yl)acrylamide (Compound 103)

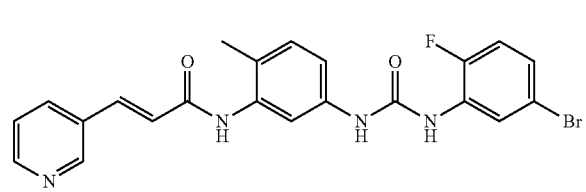 [SMILES: Cc1ccc(NC(=O)Nc2cc(Br)ccc2F)cc1NC(=O)/C=C/c1cccnc1]

The compound was synthesized by reference to example 98.

¹HNMR (DMSO-d₆) (ppm): δ2.20 (s, 3H), δ7.09-7.64 (m, 7H), δ7.77 (s, 1H), δ8.05 (d, 1H), δ8.14 (t, 1H), δ8.59 (dd, 1H), δ8.61 (d, 1H), δ8.83 (s, 1-H), δ9.14 (s, 1H), δ9.51 (s, 1H).

Example 104

N-(5-(3-(4-methoxyphenyl)ureido)-2-methylphenyl)-3-(pyridin-3-yl)acrylamide Compound 104)

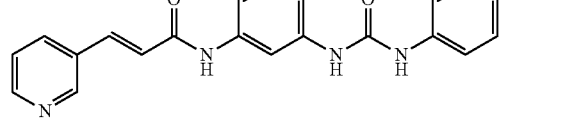

The compound was synthesized by reference to example 98.

¹HNMR (DMSO-d₆) (ppm): δ2.18 (s, 3H), δ3.71 (s, 3H), δ6.86 (d, 2H), δ7.07-7.12 (m, 2H), δ7.24 (dd, 1H), δ7.34 (d, 2H), δ7.49 (dd, 1H), δ7.61 (d, 1H), δ7.72 (s, 1H), δ8.04-8.06 (d, 1H), δ8.38 (s, 1H), δ8.58 (d, 2H), δ8.83 (s, 1H).

Example 105

N-(5-(3-(4-fluorophenyl)ureido)-2-methylphenyl)-3-(pyridin-3-yl)acrylamide (Compound 105)

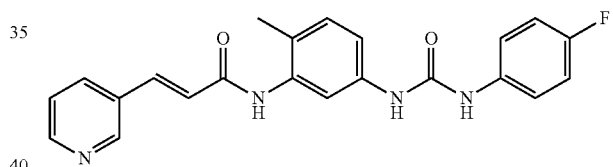

The compound was synthesized by reference to example 98.

¹HNMR (DMSO-d₆) (ppm): δ2.19 (s, 3H), δ7.09-7.26 (m, 5H), δ7.44-7.74 (m, 5H), δ8.05 (d, 1H), δ8.59 (d, 1H), δ8.67 (d, 2H), δ8.83 (s, 1H), δ9.52 (s, 1H).

Example 106

N-(5-(3-(4-chloro-3-(trifluoromethyl)phenyl)ureido)-2-methyl phenyl)-3-(pyridin-3-yl)acrylamide (Compound 106)

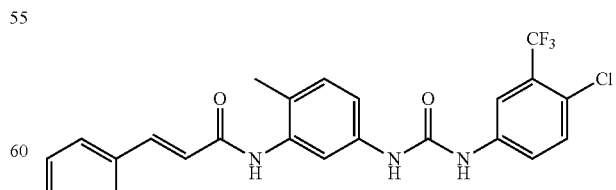

The compound was synthesized by reference to example 98.

MS (FAB): 475 (M+1)

Example 107

N-(5-(3-(4-bromo-3-(trifluoromethyl)phenyl)ureido)-2-methyl phenyl)-3-(pyridin-3-yl)acrylamide (Compound 107)

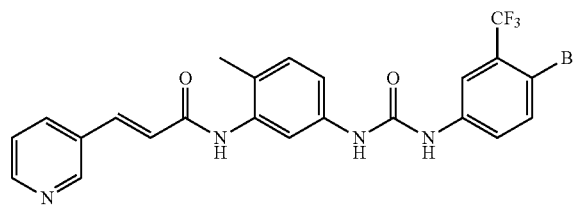

The compound was synthesized by reference to example 98.
MS (FAB): 520 (M+1)

Example 108

N-(5-(3-(3-(trifluoromethyl)-4-fluorophenyl)ureido)-2-methyl phenyl)-3-(pyridin-3-yl)acrylamide (Compound 108)

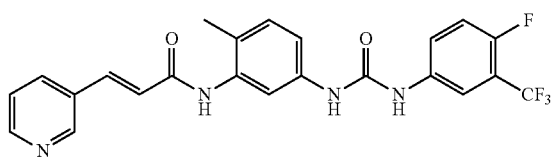 [SMILES: Cc1ccc(NC(=O)Nc2ccc(F)c(C(F)(F)F)c2)cc1NC(=O)/C=C/c1cccnc1]

The compound was synthesized by reference to example 98.
$^1$HNMR (DMSO-$d_6$) (ppm): δ2.20 (s, 3H), δ7.08-7.15 (m, 2H), δ7.23 (dd, 1H), δ7.42-7.50 (m, 2H), δ7.62 (d, 2H), δ7.76 (s, 1H), δ8.02-8.06 (m, 2H), δ8.59 (dd, 1H), δ8.79 (s, 1H), δ8.83 (d, 1H), δ8.93 (s, 1H), δ9.49 (s, 1H).

Example 109

Activity assays for Abl tyrosine protein kinase: Enzyme reaction solution includes 50 mM Tris-HCL buffer solution (pH7.5), 10 mM magnesium chloride, 1 mM EDTA, 10 uM-P marked ATP (3000-5000 cpm/pmol), 0.2 mM ATP and 10 μg Abl peptide substrate EAIYAAPFAKKK (1 mg/ml). The volume of the reaction solution is 40 μl. The reaction solution was mixed with the test compound dissolved in DMSO homogenously, and then 10 μg Abl tyrosine protein kinase (10000 units/ml, purchased from Cell Signaling Technology, USA) was added to start the enzyme reaction.

After reacting for 15 min at 30° C., 10% trichloroacetic acid solution (40 μl) was added to terminate the reaction. The reaction mixture was centrifuged for 2 min at 10,000 rpm. After that, 35 μl supernatant was sucked and added dropwise to P81 ion exchange paper (Whatman), said paper then was washed with 6% acetic acid for three times, and dried at room temperature. The dried filter paper then was placed in radiation counting vial. The radiation dose was measured on β ray counter. The activity of Abl tyrosine protein kinase was calculated according to the radiation dose on the filter paper.

The inhibitory effects of the compounds of this invention on Abl tyrosine protein kinase were expressed by the concentrations of the compounds that result in 50% enzyme activity inhibition ($IC_{50}$).

Inhibitory effects of the Compounds of the Invention on Abl tyrosine is Protein Kinase

| compound | $IC_{50}$ |
| --- | --- |
| compound 1 | 0.021 |
| compound 7 | 0.012 |
| compound 9 | 0.055 |
| STI-571 | 0.086 |

Example 110

Inhibitory Effects of the Compounds on Human Leukemia Cell K562

K562 cells were seeded in RPMI1640 cell culture solution containing 10% of fetal calf serum (supplemented with 100 ku/L of penicillin and streptomycin each). Culture dish was placed in the cell incubator under 5% of $CO_2$ at 37° C. The culture solution was centrifuged and replaced every 2-3 days to passage and collect cells.

Cells in logarithmic growth phase were formulated into the cell suspensions at the required concentration with RPMI1640 culture solution containing 10% fetal calf serum. The resulting mixture was added to 96-wells cell culture plate at 3,000 cells per well (100 μl); after 12 hours of culture, to each well was added different amount of stock solution. The final concentrations of the samples are 100 μg/ml, 10 μg/ml, 1 μg/ml, 0.10 g/ml, and 0.01 μg/ml respectively in triplicate. After 72 h~120 h, supernatant was discarded. To each well was added 201 fresh serum-free culture solution containing 5 mg/ml blue tetrazolium (MTT). After culturing for 4 hours at 37° C., the mixture was centrifuged at 3000 rpm/min and the supernatant was discarded. Formazan was dissolved with 200 μl DMSO. After vortex oscillation for 1 min, absorbance value (OD-value) was measured on microplate reader at the wavelength of 570/450 nm. Inhibition ratio=(control group OD-value−drug group OD-value)/control group OD-value× 100%.

| Inhibitory effects on Human Leukemia Cell K562 | |
| --- | --- |
| Target Compounds | $IC_{50}$ Value (μM) |
| compound 1 | <0.0027 |
| compound 2 | <0.0027 |
| compound 3 | <0.0025 |
| compound 4 | 0.002-0.02 |
| compound 5 | 0.001-0.02 |
| compound 7 | <0.001 |
| compound 10 | <0.001 |
| compound 11 | <0.002 |
| compound 12 | <0.005 |
| compound 13 | 0.002 |
| compound 19 | <0.001 |
| compound 20 | <0.001 |
| compound 21 | 0.002 |
| compound 22 | <0.001 |
| compound 23 | <0.001 |
| compound 24 | <0.001 |
| compound 25 | 0.002-0.02 |
| compound 26 | 0.002-0.02 |
| compound 31 | <0.001 |
| compound 32 | <0.001 |
| compound 33 | <0.001 |
| compound 39 | <0.001 |
| compound 42 | <0.001 |
| compound 43 | <0.001 |
| compound 44 | <0.001 |

-continued

Inhibitory effects on Human Leukemia Cell K562

| Target Compounds | IC$_{50}$ Value (μM) |
|---|---|
| compound 50 | 0.002-0.02 |
| compound 51 | <0.002 |
| compound 52 | <0.002 |
| compound 53 | <0.001 |
| compound 54 | 0.002-0.02 |
| compound 55 | <0.002 |
| compound 56 | 0.002-0.02 |
| compound 57 | 0.002-0.02 |
| compound 58 | <0.001 |
| compound 60 | <0.001 |
| compound 61 | <0.001 |
| compound 62 | <0.001 |
| compound 66 | 0.002-0.02 |
| compound 67 | 0.002-0.02 |
| compound 69 | <0.001 |
| compound 71 | <0.001 |
| compound 74 | 0.002-0.02 |
| compound 77 | <0.001 |
| compound 78 | <0.001 |
| compound 79 | 0.002-0.02 |
| compound 80 | 0.002-0.02 |
| compound 81 | <0.02 |
| compound 82 | <0.02 |
| compound 90 | <0.001 |
| compound 102 | 0.01-0.02 |
| STI-571 | 0.03 |

Conclusion: Target compounds have higher inhibitory effects on Bcr-Abl positive human leukemia cell K562 and are superior to positive drug STI-571.

I claim:

1. A compound of formula (I):

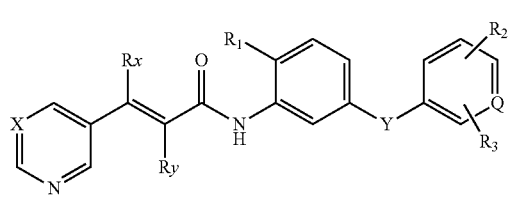

Formula (I)

or pharmaceutical acceptable salts or solvates thereof;
wherein:
R$_1$ is C$_1$-C$_4$ alkyl;
X is CH or N;
Q is CH or N;
Y is formamido

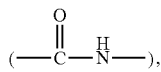

carbamoyl

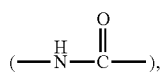

or ureido

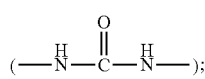

R$_x$ and R$_y$ are hydrogen or C$_1$-C$_4$ alkyl, respectively;
R$_2$, and R$_3$ are each independently hydrogen, halogen, C$_1$-C$_4$ alkyl, C$_1$-C$_4$ alkoxy, C$_1$-C$_4$ alkylamino, di-(C$_1$-C$_4$ alkyl)amino, heterocyclyl, or non-heterocyclyl.

2. The compound according to claim 1, wherein R$_1$ is methyl.

3. The compound according to claim 1, wherein R$_2$, and R$_3$ are each independently hydrogen, halogen, C$_1$-C$_4$ alkyl, C$_1$-C$_4$ alkoxy, C$_1$-C$_4$ alkylamino, di-(C$_1$-C$_4$ alkyl)amino, heterocyclyl, or non-heterocyclyl, which, except hydrogen or halogen, can be further optionally substituted by halogen, C$_1$-C$_4$ alkyl, C$_1$-C$_4$ alkoxy, di-(C$_1$-C$_4$ alkyl)amino, or heterocyclyl; optionally, these substituents can also be substituted by halogen, C$_1$-C$_4$ alkyl, C$_1$-C$_4$ alkoxy, C$_1$-C$_4$ alkylamino, di-(C$_1$-C$_4$ alkyl)amino, heterocyclyl, or non-heterocyclyl.

4. The compound according to claim 1, wherein Y is carbamoyl

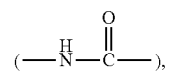

that is, said compound is a compound of the following formula:

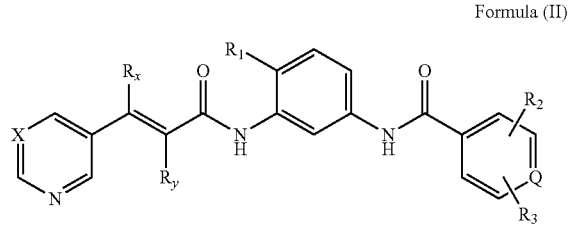

Formula (II)

or pharmaceutical acceptable salts or solvates thereof, wherein, R$_1$, R$_2$, R$_3$, R$_x$, R$_y$, X, and Q are defined in claim 1.

5. The compound of claim 4 selected from the group consisting of:
- N-(4-methyl-3-(3-(pyridin-3-yl)acrylamido)phenyl)-4-methyl benzamide;
- N-(4-methyl-3-(3-(pyridin-3-yl)acrylamido)phenyl)-4-fluorobenzamide;
- N-(4-methyl-3-(3-(pyridin-3-yl)acrylamido)phenyl)-2,4-difluoro benzamide;
- N-(4-methyl-3-(3-(pyridin-3-yl)acrylamido)phenyl)-3-(trifluoromethyl)benzamide;
- N-(4-methyl-3-(3-(pyridin-3-yl)acrylamido)phenyl)-3-chloro-4-methyl benzamide;
- N-(4-methyl-3-(3-(pyridin-3-yl)acrylamido)phenyl)-4-fluoro-3-(trifluoro methyl)benzamide;
- N-(4-methyl-3-(3-(pyridin-3-yl)acrylamido)phenyl)-2,4-dichloro benzamide;
- N-(4-methyl-3-(3-(pyridin-3-yl)acrylamido)phenyl)-3,5-bis-(trifluoromethyl)benzamide;
- N-(4-methyl-3-(3-(pyridin-3-yl)acrylamido)phenyl)-3-(trifluoromethyl)-4-methylbenzamide;
- N-(4-methyl-3-(3-(pyridin-3-yl)acrylamido)phenyl)-3-fluoro-5-(trifluoromethyl)benzamide;
- N-(4-methyl-3-(3-(pyridin-3-yl)acrylamido)phenyl)-4-((4-methyl piperazin-1-yl)methyl)benzamide;
- N-(4-methyl-3-(3-pyridin-3-yl)acrylamido)phenyl)-4-((cis-3,5-dimethyl piperazin-1-yl)methyl)benzamide;
- N-(4-methyl-3-(3-(pyridin-3-yl)acrylamido)phenyl)-4-((4-ethylpiperazin-1-yl)methyl)benzamide;
- N-(4-methyl-3-(3-(pyridin-3-yl)acrylamido)phenyl)-4-((4-piperidin-1-yl)methyl)benzamide;
- N-(4-methyl-3-(3-(pyridin-3-yl)acrylamido)phenyl)-4-(morpholin-4-ylmethyl)benzamide;

N-(4-methyl-3-(3-(pyridin-3-yl)acrylamido)phenyl)-4-((4-methyl-1,4-homopiperazin-1-yl)methyl)benzamide;
N-(4-methyl-3-(3-(pyridin-3-yl)acrylamido)phenyl)-4-((diethylamino)methyl)benzamide;
N-(4-methyl-3-(3-(pyridin-3-yl)acrylamido)phenyl)-4-((4-hydroxyethyl piperazin-1-yl)methyl)benzamide;
N-(4-methyl-3-(3-(pyridin-3-yl)acrylamido)phenyl)-4-((4-methylpiperazin-1-yl)methyl)-3-(trifluoromethyl)benzamide;
N-(4-methyl-3-(3-(pyridin-3-yl)acrylamido)phenyl)-4-((4-ethylpiperazin-1-yl)methyl)-3-(trifluoromethyl)benzamide;
N-(4-methyl-3-(3-(pyridin-3-yl)acrylamido)phenyl)-4-(morpholin-4-ylmethyl)-3-(trifluoromethyl)benzamide;
N-(4-methyl-3-(3-(pyridin-3-yl)acrylamido)phenyl)-4-(((R)-3-(dimethylamino)pyrrolidin-1-yl)methyl)-3-(trifluoromethyl)benzamide;
N-(4-methyl-3-(3-(pyridin-3-yl)acrylamido)phenyl)-4-(((S)-3-(dimethyl amino)pyrrolidin-1-yl)methyl)-3-(trifluoromethyl)benzamide;
N-(4-methyl-3-(3-(pyridin-3-yl)acrylamido)phenyl)-4-((3-(dimethylamino)pyrrolidin-1-yl)methyl)-3-(trifluoromethyl)benzamide;
N-(4-methyl-3-(3-(pyridin-3-yl)acrylamido)phenyl)-4-((4-methyl-1,4-homopiperazin-1-yl)methyl)-3-(trifluoromethyl)benzamide;
N-(4-methyl-3-(3-(pyridin-3-yl)acrylamido)phenyl)-4-((4-methylpiperazin-1-yl)methyl)-3-bromobenzamide;
N-(4-methyl-3-(3-pyridin-3-yl)acrylamido)phenyl)-4-((cis-3,5-dimethyl piperazin-1-yl)methyl)-3-bromobenzamide;
N-(4-methyl-3-(3-(pyridin-3-yl)acrylamido)phenyl)-((4-ethylpiperazin-1-yl)methyl)-3-bromobenzamide;
N-(4-methyl-3-(3-(pyridin-3-yl)acrylamido)phenyl)-4-(morpholin-4-ylmethyl)-3-bromobenzamide;
N-(4-methyl-3-(3-(pyridin-3-yl)acrylamido)phenyl)-4-((4-methyl-1,4-homopiperazin-1-yl)methyl)-3-bromobenzamide;
N-(4-methyl-3-(3-(pyrimidin-5-yl)acrylamido)phenyl)-3,5-bis-(trifluoro methyl)benzamide;
N-(4-methyl-3-(3-(pyrimidin-5-yl)acrylamido)phenyl)-4-methyl-3-(trifluoromethyl)benzamide;
N-(4-methyl-3-(3-(pyrimidin-5-yl)acrylamido)phenyl)-5-fluoro-3-(trifluoromethyl)benzamide;
N-(4-methyl-3-(3-(pyrimidin-5-yl)acrylamido)phenyl)-4-methyl benzamide;
N-(4-methyl-3-(3-(pyrimidin-5-yl)acrylamido)phenyl)-4-fluorobenzamide;
N-(4-methyl-3-(3-(pyrimidin-5-yl)acrylamido)phenyl)-2,4-difluoro benzamide;
N-(4-methyl-3-(3-(pyrimidin-5-yl)acrylamido)phenyl)-2,4-dichloro benzamide;
N-(4-methyl-3-(3-(pyrimidin-5-yl)acrylamido)phenyl)-4-((4-methyl piperazin-1-yl)methyl)benzamide;
N-(4-methyl-3-(3-(pyrimidin-5-yl)acrylamido)phenyl)-4-((4-methyl piperazin-1-yl)methyl)-3-(trifluoromethyl)benzamide;
N-(4-methyl-3-(3-(pyrimidin-5-yl)acrylamido)phenyl)-4-((4-ethyl piperazin-1-yl)methyl)-3-(trifluoromethyl)benzamide;
N-(4-methyl-3-(3-(pyrimidin-5-yl)acrylamido)phenyl)-4-(morpholin-4-ylmethyl)-3-(trifluoromethyl)benzamide;
N-(4-methyl-3-(3-(pyrimidin-5-yl)acrylamido)phenyl)-4-(((R)-3-(dimethylamino)pyrrolidin-1-yl)methyl)-3-(trifluoromethyl)benzamide;
N-(4-methyl-3-(3-(pyrimidin-5-yl)acrylamido)phenyl)-4-(((S)-3-(dimethyl amino)pyrrolidin-1-yl)methyl)-3-(trifluoromethyl)benzamide;
N-(4-methyl-3-(3-(pyrimidin-5-yl)acrylamido)phenyl)-4-((3-(dimethylamino)pyrrolidin-1-yl)methyl)-3-(trifluoromethyl)benzamide;
N-(4-methyl-3-(3-(pyrimidin-5-yl)acrylamido)phenyl)-4-((4-methyl-1,4-homopiperazin-1-yl)methyl)-3-(trifluoromethyl)benzamide;
N-(4-methyl-3-(3-(pyrimidin-5-yl)acrylamido)phenyl)-4-((4-methyl piperazin-1-yl)methyl)-3-bromobenzamide;
N-(4-methyl-3-(3-(pyrimidin-5-yl)acrylamido)phenyl)-4-((4-methyl piperazin-1-yl)methyl)-3-chlorobenzamide;
N-(4-methyl-3-(3-(pyrimidin-5-yl)acrylamido)phenyl)-4-(morpholin-4-ylmethyl)-3-bromobenzamide;
N-(4-methyl-3-(3-(pyrimidin-5-yl)acrylamido)phenyl)-4-((4-methyl-1,4-homopiperazin-1-yl)methyl)-3-bromobenzamide;
N-((3-bromo-4-methyl)phenyl)-4-methyl-3-(3-(pyrimidin-5-yl)acrylamido)benzamide;
N-((3-chloro-4-methyl)phenyl)-4-methyl-3-(3-(pyrimidin-5-yl)acrylamido)benzamide; and
N-((3-bromo-4-methyl)phenyl)-4-methyl-3-(3-(pyridin-3-yl)acrylamido)benzamide;
or pharmaceutical acceptable salts or solvates thereof.

6. The compound according to claim 1, wherein Y is formamido

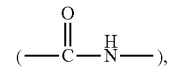

that is, said compound is a compound of the following formula:

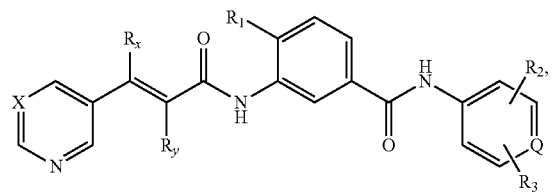

Formula (III)

or pharmaceutical acceptable salts or solvates thereof, wherein, X, $R_1$, $R_3$, $R_x$, $R_y$, and Q are defined in claim 1.

7. The compound of formula (III) of claim 6 selected from the group consisting of:
N-(3-chloro-4-fluorophenyl)-4-methyl-3-(3-(pyridin-3-yl)acrylamido)benzamide;
N-(3,5-di-(trifluoromethyl)phenyl)-4-methyl-3-(3-(pyridin-3-yl)acrylamido)benzamide;
N-(2,6-dimethyl)-4-methyl-3-(3-(pyridin-3-yl)acrylamido)benzamide;
N-(3-(trifluoromethyl)phenyl)-4-methyl-3-(3-(pyridin-3-yl)acrylamido)benzamide;
N-(4-bromo-2-fluorophenyl)-4-methyl-3-(3-(pyridin-3-yl)acrylamido)benzamide;
N-(4-(trifluoromethoxy)phenyl)-4-methyl-3-(3-(pyridin-3-yl)acrylamido)benzamide;

N-(4-(methoxy)phenyl)-4-methyl-3-(3-(pyridin-3-yl)acrylamido)benzamide;
N-(4-(4-methyl-1H-imidazol-1-yl)-3-(trifluoromethyl)phenyl)-4-methyl-3-(3-(pyridin-3-yl)acrylamido)benzamide;
N-(3,4-dichlorophenyl)-4-methyl-3-(3-(pyridin-3-yl)acrylamido)benzamide;
N-(2-chloro-5-(trifluoromethyl)phenyl)-4-methyl-3-(3-(pyridin-3-yl)acrylamido)benzamide;
N-(4-chloro-3-(trifluoromethyl)phenyl)-4-methyl-3-(3-(pyridin-3-yl)acrylamido)benzamide;
N-(3,4-dimethoxyphenyl)-4-methyl-3-(3-(pyridin-3-yl)acrylamido)benzamide;
N-(4-fluoro-3-(trifluoromethyl)phenyl)-4-methyl-3-(3-(pyridin-3-yl)acrylamido)benzamide;
N-(3-fluoro-4-methylphenyl)-4-methyl-3-(3-(pyridin-3-yl)acrylamido)benzamide;
N-(4-methyl-3-(trifluoromethyl)phenyl)-4-methyl-3-(3-(pyridin-3-yl)acrylamido)benzamide;
N-(3-(4-methyl-1H-imidazol-1-yl)-5-(trifluoromethyl)phenyl)-4-methyl-3-(3-(pyridin-3-yl)acrylamido)benzamide;
N-(4-(morpholin-4-ylmethyl)-3-(trifluoromethyl)phenyl)-4-methyl-3-(3-(pyridin-3-yl)acrylamido)benzamide;
N-(4-fluorophenyl)-4-methyl-3-(3-(pyridin-3-yl)acrylamido)benzamide;
N-(4-(methyl)phenyl)-4-methyl-3-(3-(pyridin-3-yl)acrylamido)benzamide;
N-(2-chloro-6-methylphenyl)-4-methyl-3-(3-(pyridin-3-yl)acrylamido)benzamide;
N-(3-fluorophenyl)-4-methyl-3-(3-(pyridin-3-yl)acrylamido)benzamide;
N-(4-(morpholin-4-yl)-3-(trifluoromethyl)phenyl)-4-methyl-3-(3-(pyridin-3-yl)acrylamido)benzamide;
N-((3-(piperidin-1-yl)methyl)phenyl)-4-methyl-3-(3-(pyridin-3-yl)acrylamido)benzamide;
N-(4-(4-methylpiperazin-1-yl)-3-(trifluoromethyl)phenyl)-4-methyl-3-(3-(pyridin-3-yl)acrylamido)benzamide;
N-(3-((4-methylpiperazin-1-yl)methyl)phenyl)-4-methyl-3-(3-(pyridin-3-yl)acrylamido)benzamide;
N-(4-(morpholin-4-ylmethyl)phenyl)-4-methyl-3-(3-(pyridin-3-yl)acrylamido)benzamide;
N-(4-(4-ethylpiperazin-1-yl)-3-(trifluoromethyl)phenyl)-4-methyl-3-(3-(pyridin-3-yl)acrylamido)benzamide;
N-(4-methyl-3-(trifluoromethyl)phenyl)-4-methyl-3-(3-(pyrimidin-5-yl)acrylamido)benzamide;
N-(4-(morpholin-4-yl)-3-(trifluoromethyl)phenyl)-4-methyl-3-(3-(pyrimidin-5-yl)acrylamido)benzamide;
N-(4-chloro-3-(trifluoromethyl)phenyl)-4-methyl-3-(3-(pyrimidin-5-yl)acrylamido)benzamide;
N-(3-fluoro-4-methylphenyl)-4-methyl-3-(3-(pyrimidin-5-yl)acrylamido)benzamide;
N-(3-chloro-4-fluorophenyl)-4-methyl-3-(3-(pyrimidin-5-yl)acrylamido)benzamide;
N-(2-chloro-6-methylphenyl)-4-methyl-3-(3-(pyrimidin-5-yl)acrylamido)benzamide;
N-(3,4-dichlorophenyl)-4-methyl-3-(3-(pyrimidin-5-yl)acrylamido)benzamide;
N-(4-trifluoromethoxyphenyl)-4-methyl-3-(3-(pyrimidin-5-yl)acrylamido)benzamide;
N-(3-(4-methyl-1H-imidazol-1-yl)-5-(trifluoromethyl)phenyl)-4-methyl-3-(3-(pyrimidin-5-yl)acrylamido)benzamide;
N-(4-methylphenyl)-4-methyl-3-(3-(pyrimidin-5-yl)acrylamido)benzamide;
N-(4-fluorophenyl)-4-methyl-3-(3-(pyrimidin-5-yl)acrylamido)benzamide;
N-(4-bromo-2-fluorophenyl)-4-methyl-3-(3-(pyrimidin-5-yl)acrylamido)benzamide;
N-(3-(trifluoromethyl)phenyl)-4-methyl-3-(3-(pyrimidin-5-yl)acrylamido)benzamide;
N-(3-fluorophenyl)-4-methyl-3-(3-(pyrimidin-5-yl)acrylamido)benzamide;
N-(3,5-di-(trifluoromethyl)phenyl)-4-methyl-3-(3-(pyrimidin-5-yl)acrylamido)benzamide;
N-(4-fluoro-3-(trifluoromethyl)phenyl)-4-methyl-3-(3-(pyrimidin-5-yl)acrylamido)benzamide;
N-(4-(4-methylpiperazin-1-yl)-3-(trifluoromethyl)phenyl)-4-methyl-3-(3-(pyrimidin-5-yl)acrylamido)benzamide; and
N-(4-(4-methyl-1H-imidazol-1-yl)-3-(trifluoromethyl)phenyl)-4-methyl-3-(3-(pyrimidin-5-yl)acrylamido)benzamide, or pharmaceutical acceptable salts or solvates thereof.

8. The compound according to claim 1, wherein Y is ureido

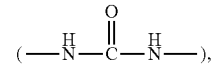

that is, said compound is a compound of the following formula:

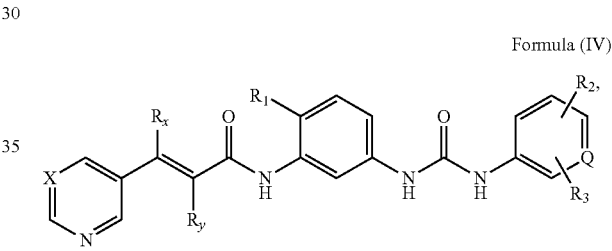

Formula (IV)

or pharmaceutical acceptable: salts or solvates thereof, wherein, X, $R_1$, $R_3$, $R_x$, $R_y$, and Q are defined in claim 1.

9. The compound of claim 8 selected from the group consisting of:
N-(5-(3-(3-trifluoromethyl)phenyl)ureido)-2-methylphenyl)-3-(pyridin-3-yl)acrylamide;
N-(5-(3-(2-chloro-5-(trifluoromethyl)phenyl)ureido)-2-methylphenyl)-3-(pyridin-3-yl)acrylamide;
N-(5-(3-(4-(trifluoromethoxy)phenyl)ureido)-2-methylphenyl)-3-(pyridin-3-yl)acrylamide;
N-(2-methyl-5-(3-(5-(methylisoxazol-3-yl)ureido)phenyl)-3-(pyridin-3-yl)acrylamide;
N-(5-(3-(3-chloro-4-fluorophenyl)ureido)-2-methylphenyl)-3-(pyridin-3-yl)acrylamide;
N-(5-(3-(5-bromo-2-fluorophenyl)ureido)-2-methylphenyl)-3-(pyridin-3-yl)acrylamide;
N-(5-(3-(4-methoxyphenyl)ureido)-2-methylphenyl)-3-(pyridin-3-yl)acrylamide;
N-(5-(3-(4-fluorophenyl)ureido)-2-methylphenyl)-3-(pyridin-3-yl)acrylamide;
N-(5-(3-(4-chloro-3-(trifluoromethyl)phenyl)ureido)-2-methylphenyl)-3-(pyridin-3-yl)acrylamide;
N-(5-(3-(4-bromo-3-(trifluoromethyl)phenyl)ureido)-2-methylphenyl)-3-(pyridin-3-yl)acrylamide; and
N-(5-(3-(3-(trifluoromethyl)-4-fluorophenyl)ureido)-2-methylphenyl)-3-(pyridin-3-yl)acrylamide, or pharmaceutical acceptable salts or solvates thereof.

10. A method for preparing the compound according to claim 1, comprising the reaction of the compound of formula (V) with the compound of formula (VI):

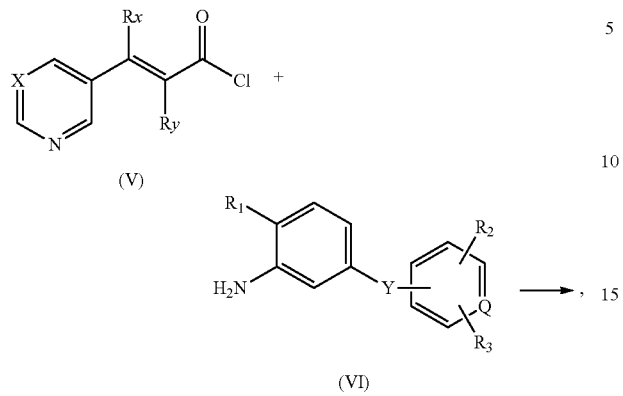

wherein, X, Y, $R_1$, $R_3$, $R_x$, $R_y$, and Q in formula (V) or (VI) are defined in claim 1.

11. A pharmaceutical composition comprising the compound of claim 1, or pharmaceutical acceptable salts or solvates thereof.

12. The compound according to claim 2, wherein Y is carbamoyl

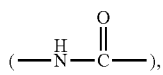

that is, said compound is a compound of the following formula:

Formula (II)

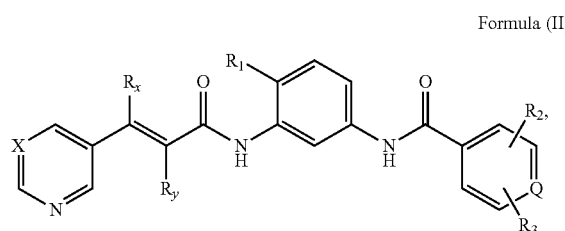

or pharmaceutical acceptable salts or solvates thereof, wherein, $R_1$, $R_2$, $R_3$, $R_x$, $R_y$, X, and Q are defined in claim 1.

13. The compound according to claim 3, wherein Y is carbamoyl

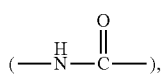

that is, said compound is a compound of the following formula: ##STR00152## or pharmaceutical acceptable salts or solvates thereof, wherein, $R_1$, $R_2$, $R_3$, $R_x$, $R_y$, X, and Q are defined in claim 1.

14. The compound according to claim 2, wherein Y is formamido

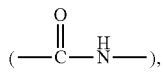

that is, said compound is a compound of the following formula:

Formula (III)

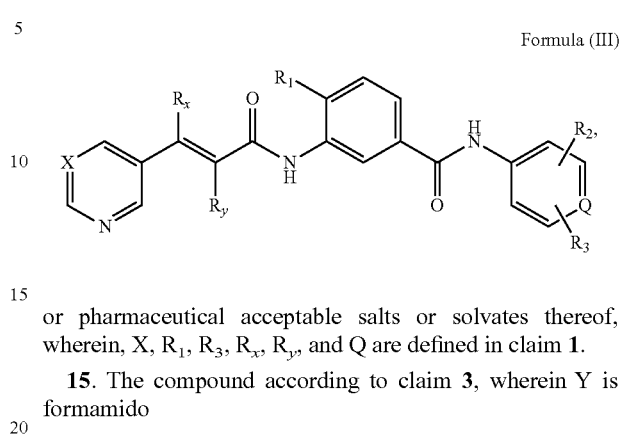

or pharmaceutical acceptable salts or solvates thereof, wherein, X, $R_1$, $R_3$, $R_x$, $R_y$, and Q are defined in claim 1.

15. The compound according to claim 3, wherein Y is formamido

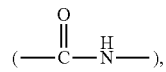

that is, said compound is a compound of the following formula:

Formula (III)

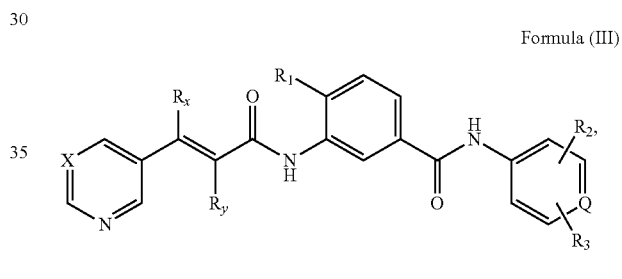

or pharmaceutical acceptable salts or solvates thereof, wherein, X, $R_1$, $R_3$, $R_x$, $R_y$, and Q are defined in claim 1.

16. The compound according to claim 2, wherein Y is ureido

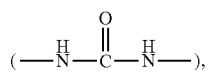

that is, said compound is a compound of the following formula:

Formula (IV)

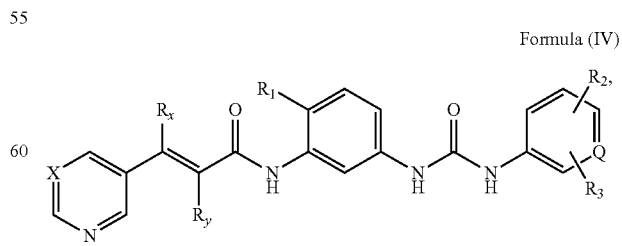

or pharmaceutical acceptable salts or solvates thereof, wherein, X, $R_1$, $R_3$, $R_x$, $R_y$, and Q are defined in claim 1.

17. The compound according to claim 3, wherein Y is ureido

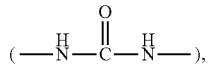

that is, said compound is a compound of the following formula:

Formula (IV)

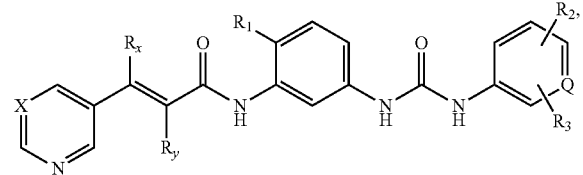

or pharmaceutical acceptable salts or solvates thereof, wherein, X, $R_1$, $R_3$, $R_x$, $R_y$, and Q are defined in claim 1.

18. A method for preparing the compound according to claim 2, comprising the reaction of the compound of formula (V) with the compound of formula (VI)

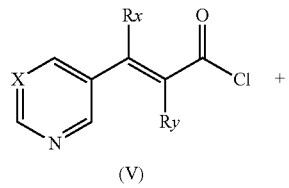

(V)

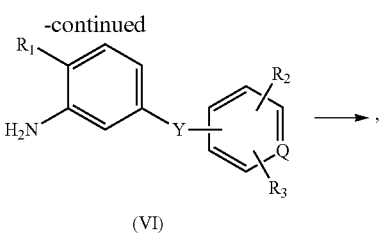

(VI)

wherein, X, Y, $R_1$, $R_3$, $R_x$, $R_y$, and Q in formula (V) or (VI) are defined in claim 1.

19. A method for preparing the compound according to claim 3, comprising the reaction of the compound of formula (V) with the compound of formula (VI)

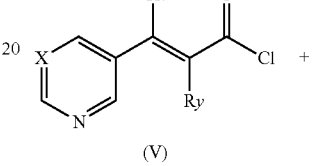

(V)

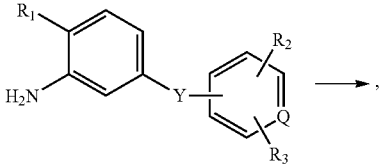

(VI)

wherein, X, Y, $R_1$, $R_3$, $R_x$, $R_y$, and Q in formula (V) or (VI) are defined in claim 1.

* * * * *